(12) United States Patent
Augustine et al.

(10) Patent No.: US 6,830,049 B2
(45) Date of Patent: *Dec. 14, 2004

(54) AIRWAY DEVICE WITH PROVISION FOR COUPLING TO AN INTRODUCER

(75) Inventors: Scott Douglas Augustine, Bloomington, MN (US); Randall Charles Arnold, Minnetonka, MN (US); Thomas Wayne McGrail, Chaska, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 114 days.

This patent is subject to a terminal disclaimer.

(21) Appl. No.: 10/154,450

(22) Filed: May 23, 2002

(65) Prior Publication Data

US 2002/0189618 A1 Dec. 19, 2002

Related U.S. Application Data

(63) Continuation-in-part of application No. 09/199,540, filed on Nov. 25, 1998, now Pat. No. 6,427,686, which is a continuation-in-part of application No. 08/730,791, filed on Oct. 16, 1996, now Pat. No. 5,937,859.

(51) Int. Cl.[7] .............................................. A61M 16/00
(52) U.S. Cl. ............................ 128/207.15; 128/200.26; 128/207.14
(58) Field of Search ............. 128/200.26, 207.13–207.15, 128/207.18; 606/136, 108, 156; 600/185, 190, 194, 195

(56) References Cited

U.S. PATENT DOCUMENTS

| | | | | |
|---|---|---|---|---|
| 614,854 A | * | 11/1898 | Kratzmueller | |
| 724,046 A | * | 3/1903 | Sampson | |
| 3,154,069 A | * | 10/1964 | Ring | |
| 3,930,507 A | * | 1/1976 | Berman | |
| 4,054,135 A | * | 10/1977 | Berman | |
| 4,067,331 A | * | 1/1978 | Berman | |
| 4,068,658 A | * | 1/1978 | Berman | |
| 4,069,820 A | * | 1/1978 | Berman | |
| 4,211,234 A | * | 7/1980 | Fisher | |

(List continued on next page.)

FOREIGN PATENT DOCUMENTS

| | | |
|---|---|---|
| DE | P44 47 186.6 | 12/1994 |
| DE | P44 47 186.6 | 7/1996 |

(List continued on next page.)

OTHER PUBLICATIONS

PCT International Search Report for PCT/US97/16838 dated Mar. 13, 1998.
International Search Report for PCT/US97/16838.
Partial Search Report for PCT/US99/23269.
Search Report for PCT/US99/23269.
Augustine Medical Phaise IV GO$_2$ Beta Test Documents.

*Primary Examiner*—Henry Bennett
*Assistant Examiner*—Mital Patel
(74) *Attorney, Agent, or Firm*—INCAPLAW; Terrance A. Meador

(57) ABSTRACT

A laryngeal airway device for sealing against the laryngeal opening includes an air tube with proximal and distal ends and a sealing member attached to the distal end. The airway device includes a tubular extension or snout for delivering air directly into the laryngeal opening; the snout is tapered and "hooded" in a manner that facilitates effective positioning of the airway device. The sealing member includes a coupler for coupling the device to an introducer. Complementing the laryngeal airway device is an introducer that includes a track for receiving the coupler of the laryngeal airway device and guiding the sealing member to a sealing position with respect to the laryngeal inlet.

23 Claims, 21 Drawing Sheets

U.S. PATENT DOCUMENTS

| | | | |
|---|---|---|---|
| 4,329,983 A | * | 5/1982 | Fletcher |
| 4,351,342 A | | 9/1982 | Wiita et al. |
| 4,509,514 A | | 4/1985 | Brain |
| 4,672,960 A | * | 6/1987 | Frankel |
| 4,727,872 A | * | 3/1988 | Hawk |
| 4,825,858 A | * | 5/1989 | Frankel |
| 4,832,020 A | * | 5/1989 | Augustine |
| 4,949,716 A | * | 8/1990 | Chenoweth |
| 4,976,261 A | * | 12/1990 | Gluck et al. |
| 4,982,729 A | * | 1/1991 | Wu |
| 4,995,388 A | * | 2/1991 | Brain |
| 5,038,766 A | * | 8/1991 | Parker |
| 5,042,469 A | * | 8/1991 | Augustine |
| 5,092,314 A | * | 3/1992 | Zeitels |
| 5,174,283 A | * | 12/1992 | Parker |
| 5,178,132 A | * | 1/1993 | Mahefky |
| 5,203,320 A | * | 4/1993 | Augustine |
| 5,241,956 A | | 9/1993 | Brain |
| 5,259,371 A | | 11/1993 | Tonrey ................ 128/200.26 |
| 5,277,178 A | * | 1/1994 | Dingley |
| 5,287,848 A | * | 2/1994 | Cubb et al. |
| 5,303,697 A | | 4/1994 | Brain |
| 5,305,743 A | * | 4/1994 | Brain |
| 5,329,940 A | * | 7/1994 | Adair |
| 5,355,879 A | | 10/1994 | Brain |
| 5,363,838 A | * | 11/1994 | George |
| 5,443,063 A | * | 8/1995 | Greenberg |
| 5,477,851 A | * | 12/1995 | Callaghan et al. |
| 5,494,029 A | * | 2/1996 | Lane et al. |
| 5,498,231 A | * | 3/1996 | Franicevic |
| 5,509,408 A | * | 4/1996 | Kurtis |
| 5,513,627 A | | 5/1996 | Flam |
| 5,529,582 A | | 6/1996 | Fukuhara |
| 5,584,290 A | | 12/1996 | Brain |
| 5,623,921 A | | 4/1997 | Kinsinger et al. |
| 5,632,271 A | | 5/1997 | Brain |
| 5,638,813 A | * | 6/1997 | Augustine |
| 5,655,528 A | | 8/1997 | Pagan .................... 28/207.14 |
| 5,682,880 A | * | 11/1997 | Brain |
| 5,850,832 A | * | 12/1998 | Chu |
| 5,896,858 A | * | 4/1999 | Brain |
| 5,937,859 A | * | 8/1999 | Augustine et al. |
| 5,983,897 A | * | 11/1999 | Pagan |
| 5,988,167 A | * | 11/1999 | Kamen |
| 6,003,510 A | * | 12/1999 | Annunta |
| 6,012,452 A | * | 1/2000 | Pagan |
| 6,053,166 A | * | 4/2000 | Gomez |
| 6,070,581 A | * | 6/2000 | Augustine et al. |
| 6,119,695 A | * | 9/2000 | Augustine et al. |
| 6,427,686 B2 | | 8/2002 | Augustine et al. |

FOREIGN PATENT DOCUMENTS

| | | | |
|---|---|---|---|
| EP | 0 389 272 A2 | | 3/1990 |
| EP | 0 389 272 A2 | | 9/1990 |
| EP | 0 533 371 A2 | | 9/1992 |
| EP | 0 533 371 A2 | | 3/1993 |
| GB | 478958 | * | 1/1938 |
| WO | WO 95/32754 | | 12/1995 |
| WO | WO95/32754 | | 12/1995 |
| WO | WO97/12640 | | 4/1997 |
| WO | WO 97/12640 | | 4/1997 |
| WO | WO 97/12641 | | 4/1997 |
| WO | WO97/12641 | | 4/1997 |
| WO | WO98/16273 | * | 4/1998 |
| WO | WO 98/16273 | | 4/1998 |
| WO | WO 98/50096 | | 11/1998 .......... A61M/16/00 |
| WO | WO98/50096 | | 11/1998 |

* cited by examiner

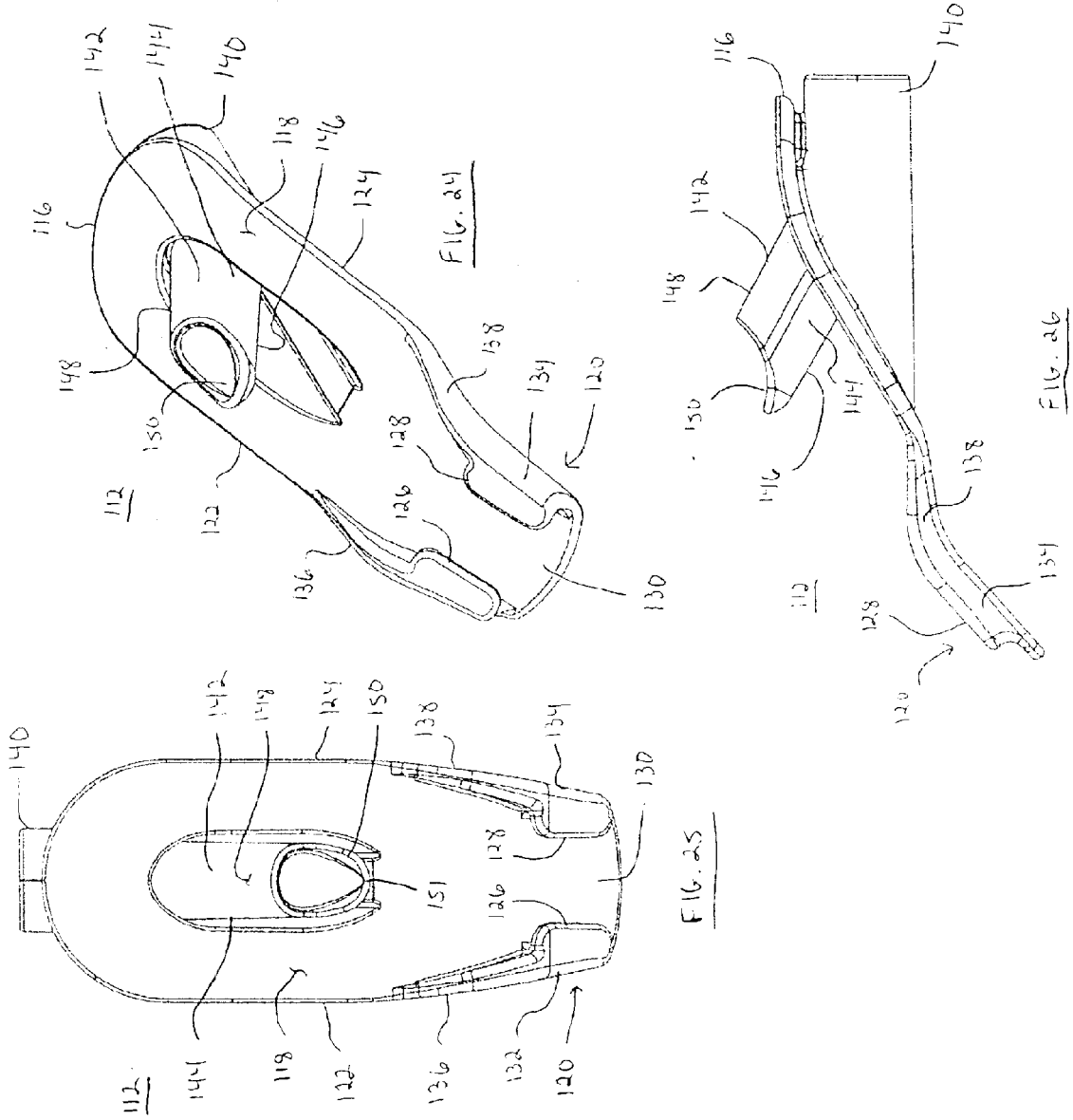

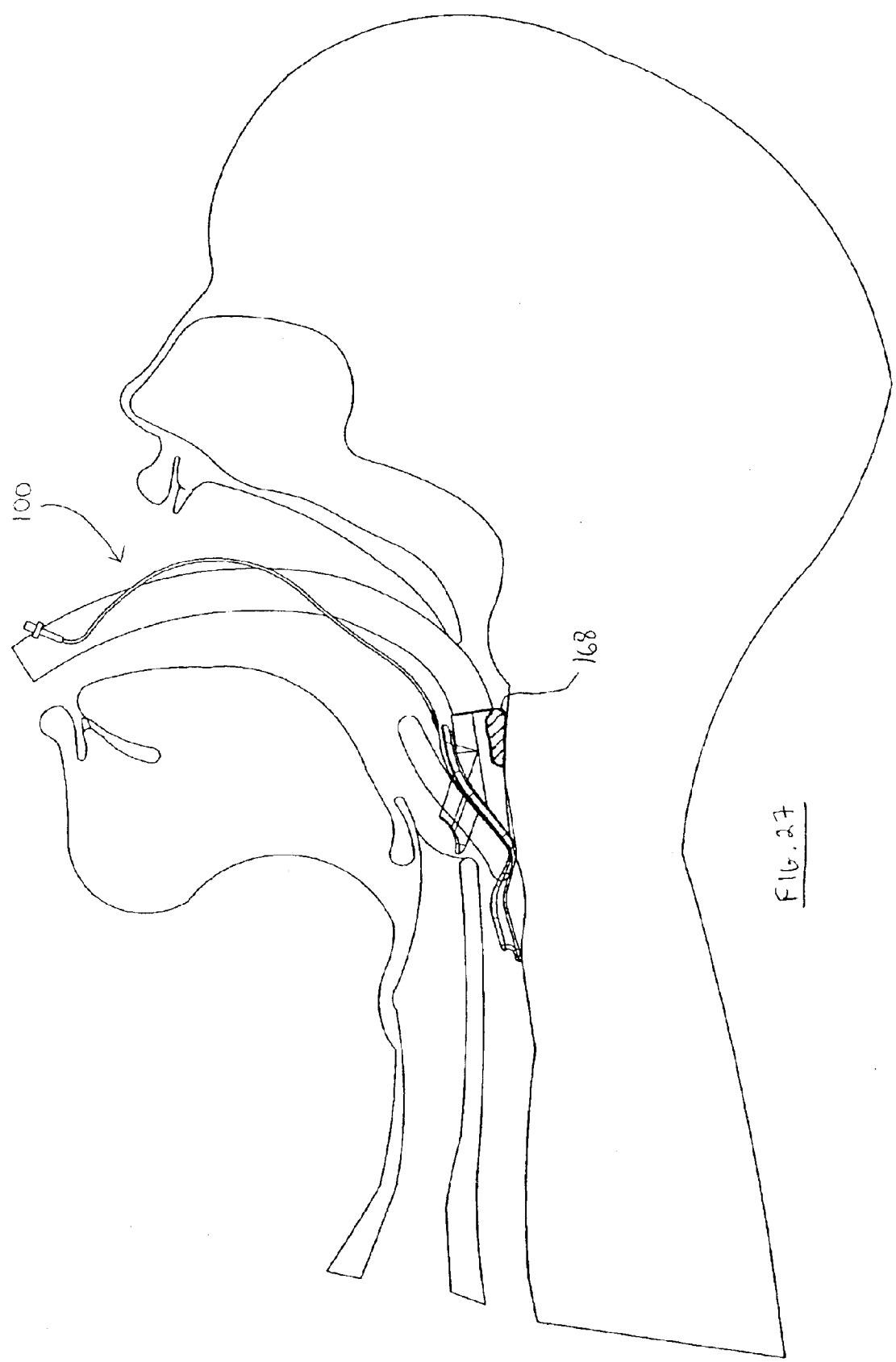

AIRWAY DEVICE WITH PROVISION FOR COUPLING TO AN INTRODUCER

CROSS-REFERENCE TO RELATED APPLICATIONS

This application is a continuation-in-part of U.S. patent application Ser. No. 09/199,540, filed Nov. 25, 1998, now U.S. Pat. No. 6,427,686 which is a continuation-in-part of U.S. patent application Ser. No. 08/730,791, filed Oct. 16, 1996, now U.S. Pat. No. 5,937,859.

This application contains subject matter that is related to the following patent applications:

U.S. patent application Ser. No. 08/885,682, filed Jun. 30, 1997, now U.S. Pat. No. 6,070,581, titled LARYNGEAL AIRWAY DEVICE;

PCT application number US 97/16838, filed Sep. 24, 1997, published Apr. 23, 1998 as WO 98/16273, titled LARYNGEAL AIRWAY DEVICE;

U.S. patent application Ser. No. 09/566,652, filed May 8, 2000, now U.S. Pat. No. 6,338,343, titled AIRWAY DEVICE WITH PROVISION FOR LATERAL ALIGNMENT, DEPTH POSITIONING, AND RETENTION IN AN AIRWAY; and U.S. patent application Ser. No. 09/199,909, filed Nov. 25, 1998, now U.S. Pat. No. 6,119,695, titled AIRWAY DEVICE WITH PROVISION FOR LATERAL ALIGNMENT, DEPTH POSITIONING, AND RETENTION IN AN AIRWAY.

The content of the above applications and patents is incorporated by reference herein.

FIELD OF THE INVENTION

The present invention relates generally to laryngeal airway devices. More particularly, the present invention relates to a laryngeal airway device that can be coupled to an introducer and guided into position in the throat.

BACKGROUND OF THE INVENTION

The prior art is replete with devices and equipment for the management of a human airway in order to control respiration. For example, an airway device facilitates ventilation of the lungs of a person. The purpose of such a device is to provide an air pathway from an external air source, through the mouth, throat, and trachea, to the lungs. Additionally, some airway devices provide a seal with the throat of a person, which allows positive pressure ventilation and which may also prevent the leakage of stomach contents into the trachea (aspiration).

It is useful to divide airway devices into two categories: those that pass through the vocal chords and are commonly referred to as "tracheal tubes," and those that lodge in the throat, above the vocal chords, and are commonly referred to as "airways." As used herein, an "airway" refers to a device that provides a fluid pathway from outside the mouth of a person to a location above the vocal chords.

In the variety of airway devices that are available, some merely support the tissue of the pharynx (throat), particularly the tongue, creating a passageway so that air can pass by and into the pharyngeal space toward the laryngeal opening, which is the opening into the voice box. Other airway devices include a tube that provides an air channel to a location near the laryngeal opening. Still other airway devices add a sealing means to the distal end of the tube in order to provide some degree of sealing between the tube and the natural airway of the person.

A laryngeal mask is an example of a sealing airway device. U.S. Pat. Nos. 4,509,514, 4,995,388, and 5,355,879 disclose laryngeal masks. A laryngeal mask includes an inflatable doughnut-shaped balloon which, when inflated, circles the laryngeal opening and creates a fluid seal between the outside of the inflated balloon and the tissues in the pharyngeal structures of the throat that surround the larynx.

The cross-referenced patent applications and issued patents (all assigned to the assignee of this application and incorporated in their entirety by this reference) disclose various airway devices, each including a sealing member mounted near the distal end of an airway tube to seal directly with the rim of the laryngeal opening, including the epiglottis, aryepiglottic folds, and arytenoid cartilages. This type of airway design creates a fluid seal directly with the larynx.

Accurate placement of an airway device can be a very difficult task for the clinician and a traumatic event for the patient. When a patient is under anesthesia, or has lost consciousness for other reasons, the tongue and tissues of the throat relax and fall back, effectively obstructing the flow air from the mouth or nose to the laryngeal opening. This same relaxation of the tongue makes it difficult to pass an airway device along the back of the tongue, into the throat. Frequently, the clinician's fingers must be inserted into the patient's mouth to displace the tongue or push the airway device around the corner at the posterior pharynx. Furthermore, the highly variable and extremely flexible anatomy surrounding the larynx make accurate positioning of an airway device very difficult. In particular, the epiglottis must be correctly positioned in order to introduce and seat an airway device that effectively seals against the laryngeal opening. An epiglottis that covers the larynx will prevent proper ventilation. Finally, the mucosal tissues lining the mouth, throat, and larynx are very fragile. Devices that are inserted blindly frequently scrape these tissues causing bleeding, sore throats, and throat infections.

SUMMARY OF THE INVENTION

A sealing laryngeal airway device forms a fluid seal against the rim of the laryngeal opening, that is, against the larynx itself. An airway device configured in accordance with the present invention includes features designed to enhance the seal against the laryngeal opening and to make insertion and alignment of the airway device easier for the clinician.

The above and other aspects of the present invention may be carried out in one form by a laryngeal airway device comprising an air tube having a first end and a second end, the air tube defining an airway, and a sealing member mounted to the air tube proximate the first end. The sealing member includes a support member having an anterior support surface, and a tubular extension protruding beyond the anterior support surface, the tubular extension further defining the airway, where the tubular extension terminates at a cupped lip.

The above and other aspects of the present invention may be carried out in another form by a laryngeal airway device comprising an air tube having a first end and a second end, and a sealing member mounted to the air tube proximate the first end. The sealing member includes a support member having an anterior support surface, a compressible pad, and an inflatable balloon positioned between the anterior support surface and the compressible pad.

BRIEF DESCRIPTION OF THE DRAWINGS

A more complete understanding of the present invention may be derived by referring to the detailed description and claims when considered in conjunction with the following Figures, wherein like reference numbers refer to similar elements throughout the Figures.

FIG. 24 is a perspective view of the support member utilized by the laryngeal airway device of FIG. 22.

FIG. 25 is a top plan view of the support member of FIG. 24.

FIG. 26 is a side elevation view of the support member of FIG. 24.

FIG. 27 is a schematic side cross-sectional representation of the anatomy of the throat showing the position of the laryngeal airway device of FIG. 22 prior to sealing with the laryngeal opening.

DETAILED DESCRIPTION OF A PREFERRED EMBODIMENT

A laryngeal airway device is designed to form a fluid seal against and within the rim of the laryngeal opening. Because the seal is against and within the rim of the larynx itself, and not with the pharyngeal structures surrounding the larynx, introduction and positioning of the device must be very accurate. A laryngeal airway device according to the present invention can be easily introduced, positioned, and sealed. It should be noted that the mechanisms and techniques that track or guide the laryngeal airway device to the laryngeal inlet could also work well with other airway devices, including a pharyngeal airway device. Therefore, although the following description is directed to a laryngeal airway device, the application of the invention is not limited to such embodiments.

Figure 1:
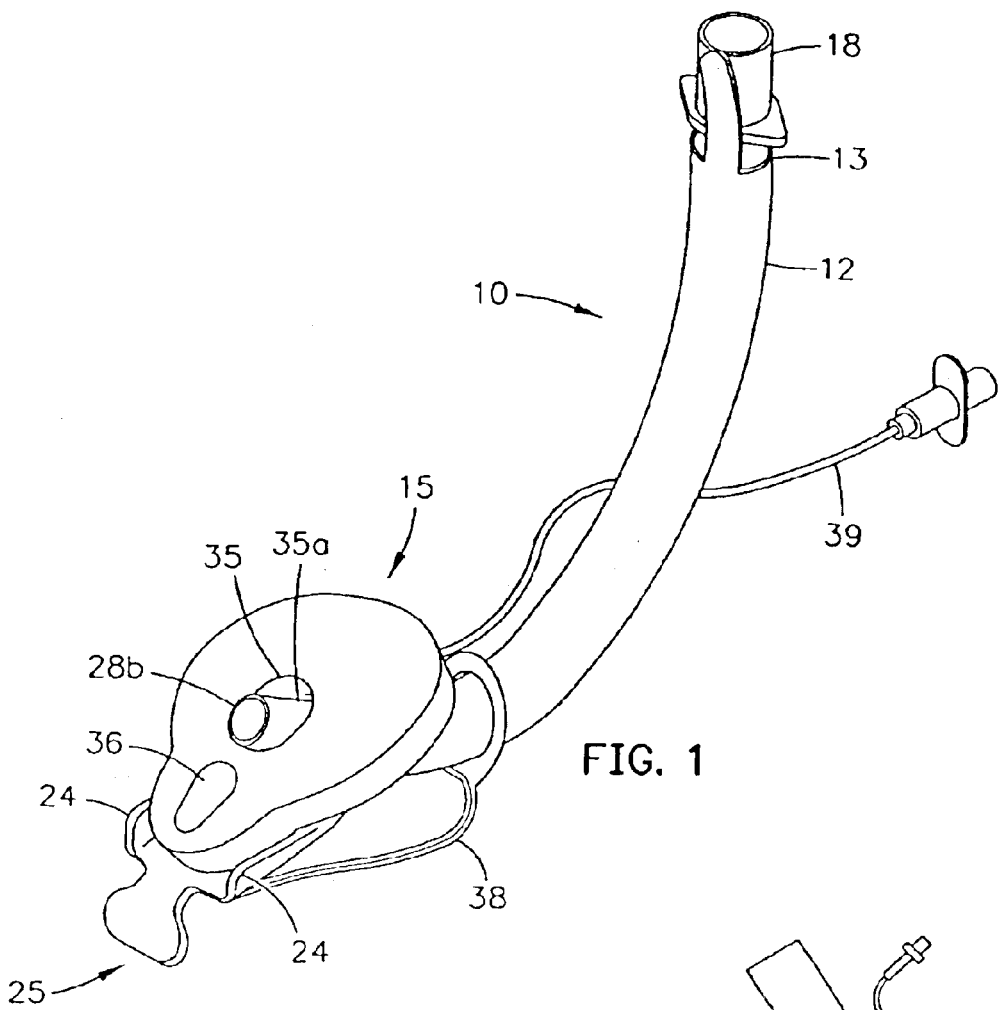
FIG. 1 is a perspective view of a laryngeal airway device having a coupler for engaging an introducer.
Figure 3:
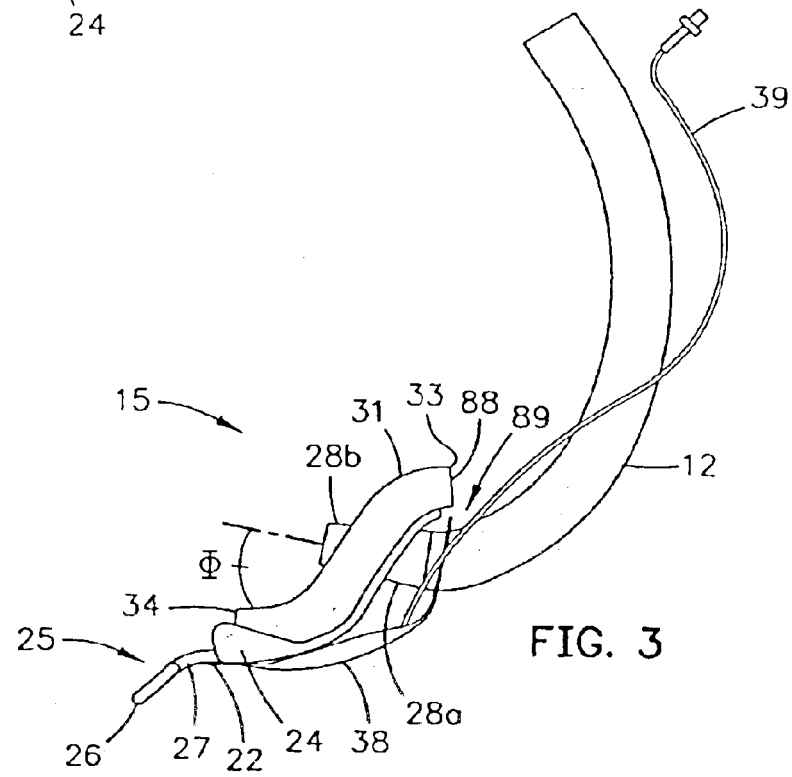
FIG. 3 is a side elevation view of the laryngeal airway device of FIG. 1.
Figure 2:
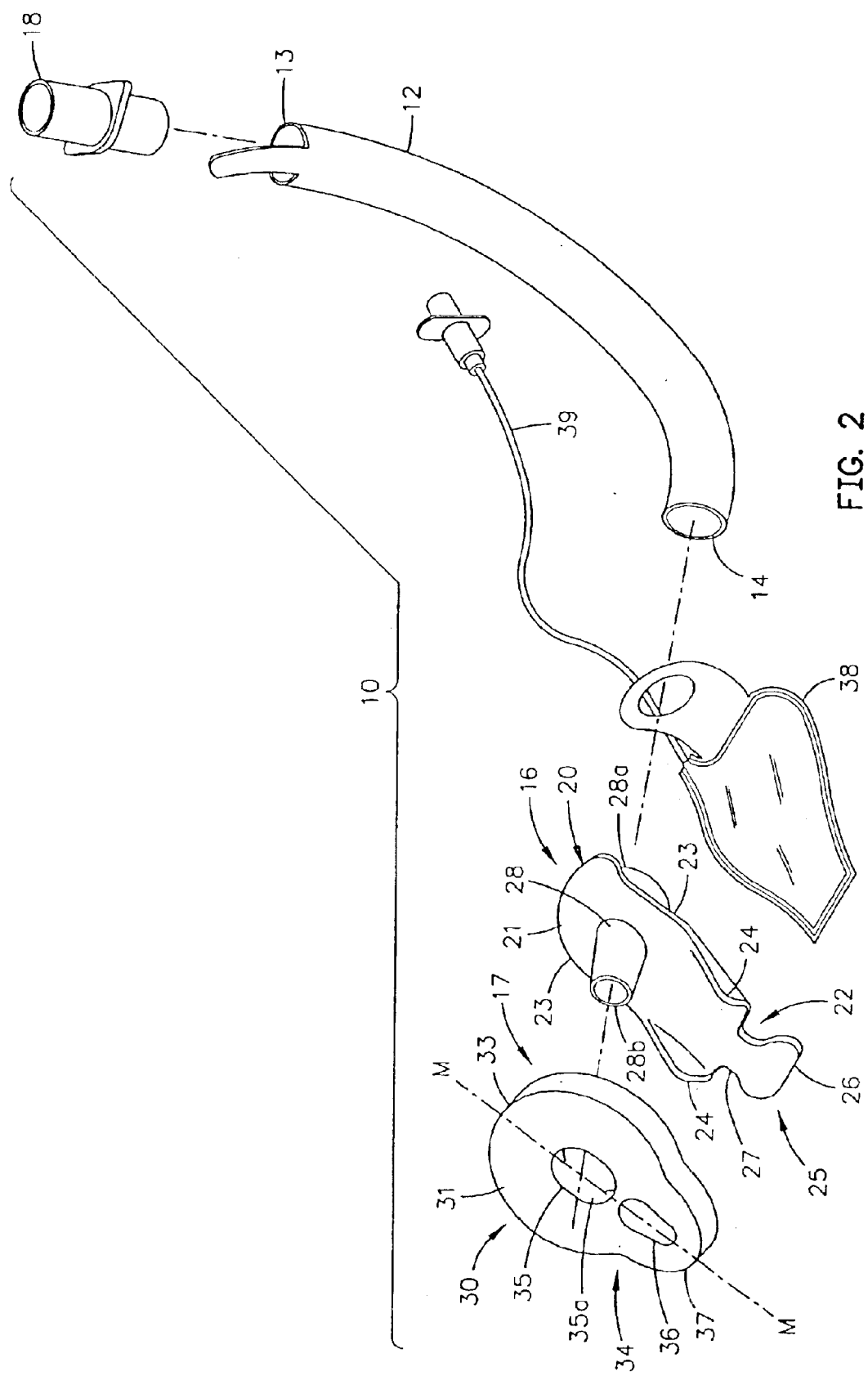
FIG. 2 is an exploded view of the laryngeal airway device of FIG. 1.
Figure 4:
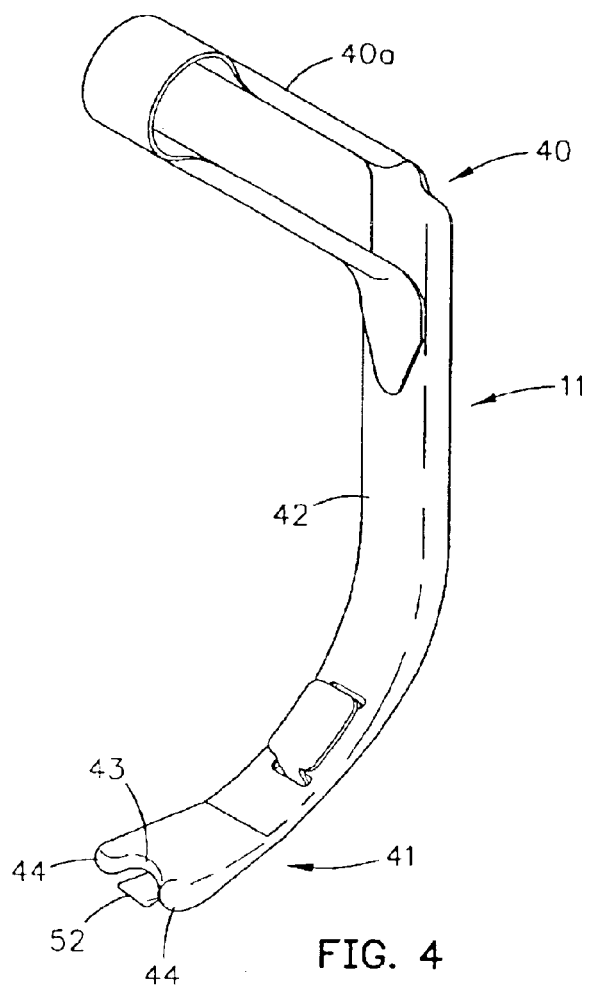
FIG. 4 is a perspective view of an introducer suitable for use with the laryngeal airway device of FIG. 1.
Figure 5:
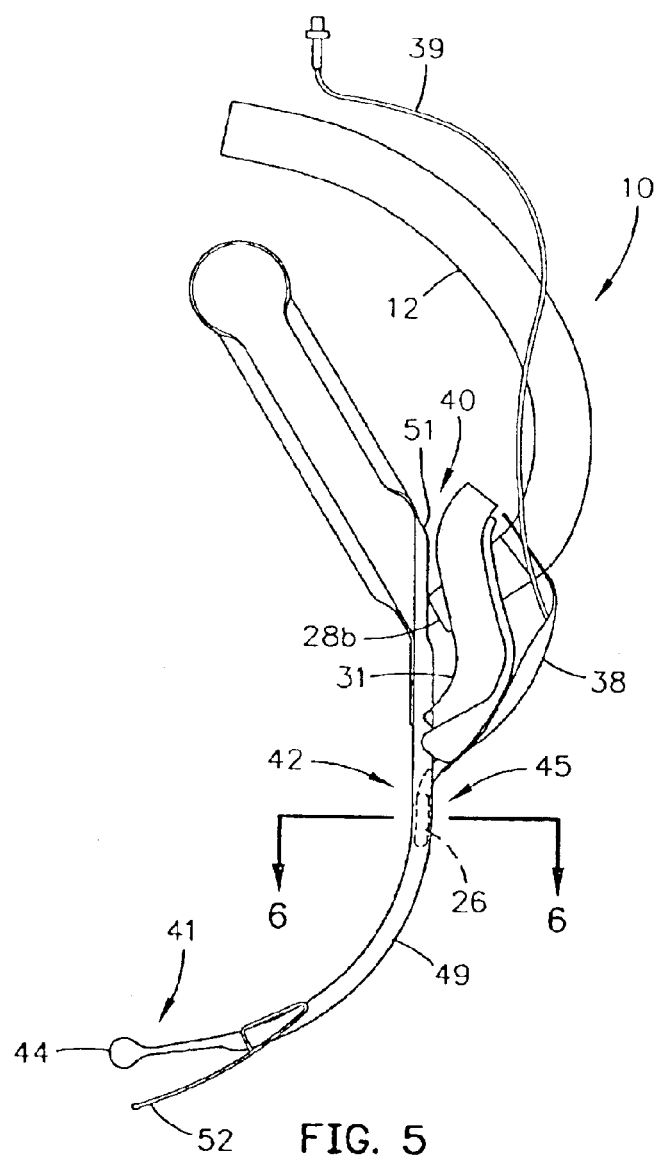
FIG. 5 is a side elevation view of the laryngeal airway device of FIG. 1 coupled to the introducer of FIG. 4.
Figure 7:
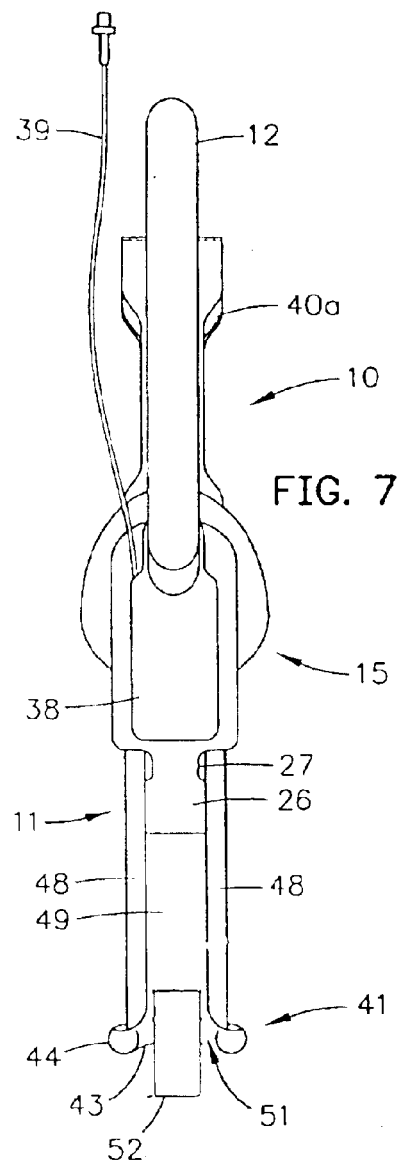
FIG. 7 is a plan view of the posterior side of the laryngeal airway device of FIG. 1 coupled to the introducer of FIG. 4.
Figure 6:
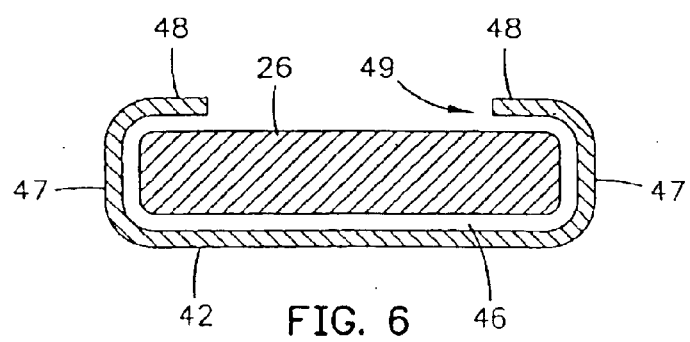
FIG. 6 is a sectional drawing taken along line 6—6 of FIG. 5.

FIGS. 1-3 illustrate an example of a laryngeal airway device 10 that incorporates several features common to the preferred embodiment of the present invention. The laryngeal airway device 10 includes a flexible air tube 12 having first (proximal) and second (distal) ends 13 and 14, respectively. The tube 12 has a curved shape that conforms to the contour of the back of the tongue. A connector 18 is attached to the proximal end 13 to connect the tube to a ventilating means, which is not shown. A sealing member 15 is attached to the tube 12 near its distal end 14. The sealing member 15 includes a support member 16 and a compressible foam pad 17.

In more detail, the support member 16 has an upper (proximal) edge 20 and an anterior support surface 21, a distal end 22, and sides 23. The anterior support surface 21 has a generally sigmoid shape in a longitudinal section. In a lateral section, the shape of the anterior support surface 21 is generally flat, although there may be some variation to accommodate design, manufacturing, or operational considerations. The lower (distal) third of anterior support surface 21 extends to the distal end 22. Laterally of the distal end 22 are a pair of opposing cricoid retainers embodied as lateral flanges 24 that rise upwardly along the sides 23 from the distal portion of the anterior support surface 21. A coupler or track-engaging mechanism is provided in the distal portion of the support member 16. In these figures, this mechanism is embodied as a flexible track-engaging flange 25 that extends forwardly of the distal end 22. The flexible track-engaging flange 25 may perform a number of useful functions, e.g., esophageal tracking and coupling to an introducer. Both of these functions are described below. The structure of the flexible track-engaging flange 25 includes a tab 26 that is connected to the distal end 22 by a pedestal 27. The lateral extent of the tab 26 at its widest section is preferably less than the width of the distal end 22 of the support member 16. The pedestal 27 is narrower than both the tab 26 and the distal end 22. The air tube 12 is enabled to project through the anterior support surface 21 of the support member 16 by a tubular, "snout-like" extension 28 that is a hollow cylinder having proximal and distal ends 28a and 28b, respectively. The tubular extension 28 is fixed to the support member 16 and the distal end 14 of the air tube 12 is received and fixed in the proximal end 28a of the tubular extension 28. The tubular extension 28 has a generally conical-like shape, with the narrower radius found at the distal end 28b and the wider radius at the proximal end 28a. The tubular extension may also be entirely cylindrical, or partially tubular, resembling a hood (as utilized by the embodiment shown in FIG. 22). Manifestly, the tubular extension 28 may be a shaped, molded portion of the air tube 12, or a piece that is separate altogether from the air tube 12 but attached to the distal end 14. The tubular extension 28 may also be slit to allow passage of an endotracheal tube.

The compressible pad 17 preferably has a pear-like shape with an upper, or proximal portion 30, an anterior surface 31, and a lower or distal portion 34. The upper portion 30 is relatively wider than the lower portion 34. The compressible pad has an anterior surface 31. The upper portion 30 includes a hole 35 defining a passageway 35a in the sealing member 15 that is centered in the upper portion 30 and on a longitudinal midline M of the pad 17. The hole 35 opens through the anterior surface 31 and the passageway 35a extends through the pad 17, aligned longitudinally with the distal end 14 of the air tube 12. The tubular extension 28 is disposed in the passageway 35a. A slot, elongated hole, notch, or depression 36 is provided in the anterior surface 31, preferably centered on the midline M, and positioned between the hole 35 and a distal end 37 of the compressible pad 17. The length of the compressible pad 17 that extends from a proximal end 33 to the distal end 37 is such that, when the pad 17 is joined to the support member 16, the distal end 37 of the pad is positioned between the lateral flanges 24, set back from the distal end 22. This leaves open a channel defined laterally between distal portions of the lateral flanges 24 and longitudinally between the distal end 37 of the compressible pad 17 and the distal end 22 of the support member.

Preferably, and for illustration and example only, the support member 16 is a flexible plastic part that maybe fabricated by molding 85 durometer PVC material. In this case, the air tube 12 should be made of somewhat stiffer material, for example 90 durometer plastic. The anterior support surface 21 has the generally sigmoid shape described above. Alternate embodiments of the anterior support. surface 21 may be substantially flat, convex, or concave in longitudinal section.

The compressible pad 17 is preferably made by molding a closed cell foam having a density of about seven pounds to make the pad soft and conformable. When the compressible pad 17 is integrated with the support member 16, its anterior surface 31 takes on the sigmoid shape of the support member's anterior support surface 21. That is, the anterior surface 31 has a sigmoid contour imposed on it in a longitudinal section, but is substantially flat in opposing lateral sections that extend from the midline M laterally to the sides of the pad 17.

The sealing member 15 may be fabricated by molding or die cutting the elements 16 and 17 and then combining them into a unitary structure by attaching the pad 17 to the anterior surface 21 of the support member 16 by gluing, heat bonding, or ultrasonic bonding, by some form of riveting, by a combination of any of these methods, or by any other equivalent that will yield an integrated, unitary structure in which the foam pad 17 has a soft, compressible characteristic, while the support member 16 is relatively more rigid than the pad 17, yet with a flexibility in one or more of its elements that allows bending during use.

Although the sealing member 15 is illustrated and described as comprising two parts, it should also be evident that, with a selection of materials and methods, this member can comprise one part with two portions in which the materials and structures of one portion transition continuously or abruptly to the materials and structures of the other portion.

As is best seen in FIG. 3, an inflatable balloon 38 is disposed on the posterior side of the support member 16, extending generally between the proximal end 28a of the tubular extension 28 and the distal end 22 of the support member 15. A small tube 39 is provided for inflating the balloon 38. The balloon 38 may be provided to compensate for unusual variations in airway anatomy. It will not be necessary to inflate the balloon 38 in all patients in order to effect an airway seal.

Refer now to FIGS. 4-7, which illustrate an introducer with which the laryngeal airway device of FIGS. 1-3 is used. The introducer, indicated generally by reference number 11, is a relatively stiff plastic or metal blade-like device having a straight portion and a curved portion. Preferably, though not necessarily, the shape may be that of a capital "J." A first (proximal) end 40 of the introducer 11 transitions to a generally elongate proximal section with an anterior surface 42 and a posterior side 45. A handle 40a is provided at the proximal end 40. A second (distal) end 41 terminates the sharp "hook-shaped" portion of the "J"-shape of the introducer. Preferably, the introducer 11 is substantially flattened in cross-section. Preferably, although not necessarily, the distal end 41 includes an indentation 43 on either side of which is a rounded protuberance 44. The indentation 43 is designed to accommodate the midline hyo-epiglottic ligament, while the protuberances 44 are designed to engage under the hyoid bone for accurate positioning of the introducer 11. These means of positioning have been described in U.S. Pat. No. 4,832,020 and U.S. Pat. No. 5,042,469, which are owned by the assignee and incorporated by this reference.

FIGS. 1, 5, 6, and 7 illustrate elements of the device 10 and the introducer 11 that permit these two elements to operate cooperatively in solving the problem of tracking or guiding the device 10 into alignment with the laryngeal opening. The flexible track-engaging flange 25 on the distal end 22 of the sealing member 15 couples to a track 46 formed on the posterior side of the introducer 11. As shown best in FIGS. 5-7, the track 46 includes two opposing slide rails that are generally "U"-shaped and are formed by upwardly-extending wall portions 47, which extend longitudinally on the posterior side 45. The wall portions 47 transition to medially-extending sections 48. There is a gap 49 between the medially-extending sections 48.

The device 10 is coupled to the introducer 11 by orienting the compressible anterior surface 31 of the sealing mechanism toward the posterior side of the introducer 11 and inserting the flange 25 between the "U"-shaped slide rails on the posterior side of the introducer 11 where the rails begin near the proximal end 40. The opening 49 captures the edges of pedestal 27, while the tab 26 of the flange 25 is retained between the slide rails. When the device is pushed toward the distal end 41 of the introducer 11, the air tube 12 is rotated to place the distal end 28b of the tubular extension 28 toward the posterior side, within the opening 49 between the slide rails. When pressure directed toward the sealing member 15 is applied on the tube 12, the device is advanced, sealing member 15 first, along the posterior side of the introducer 11 towards its distal end 41. When the flange 25 emerges from between the slide rails at the opening 51 where the medially-facing portions 48 of the slide rails taper toward the vertical portions 47, the flange 25 is released from the rail track of the introducer 11 and the device 10 is uncoupled from the introducer 11.

Figure 8:
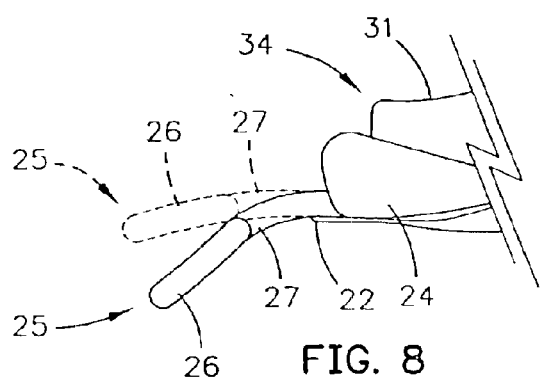
FIG. 8 is a magnified side view of a portion of the distal end of the laryngeal airway device of FIG. 1.

In this particular construction of the device 10, and as illustrated in FIG. 8, the material of which the support member 16 is made imparts a flexibility that permits the flange 25 to rotate between a first position indicated by the solid lines in FIG. 8 and a second position that is indicated by the dashed line in FIG. 8. In the first position, the device 10 is not coupled to the introducer 11. However, in the second position, the flange 25 has been engaged between the slide rails of the introducer 11 and the device 10 has been advanced to the point just before the flange 25 is released.

Positioning of the Laryngeal Airway Device

Figure 9:
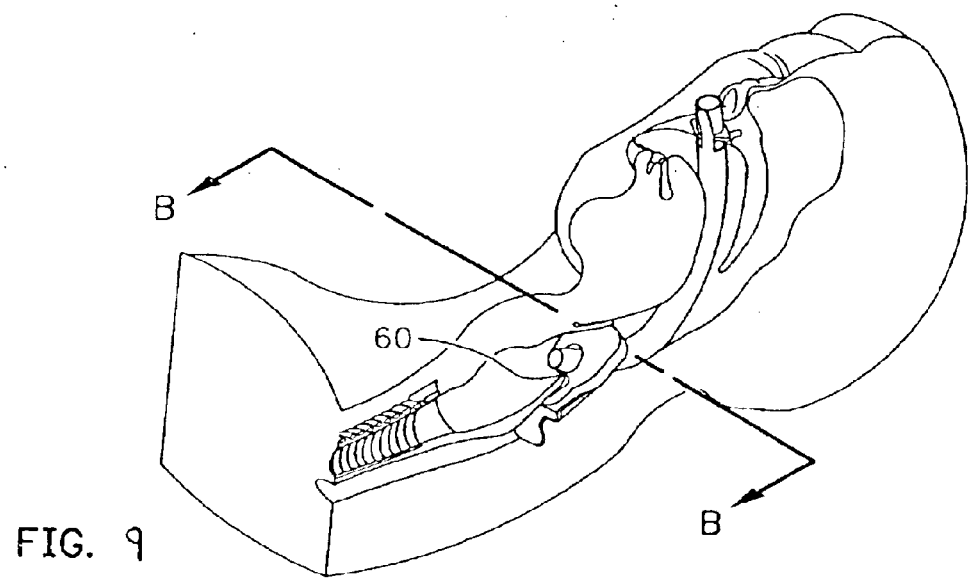
FIG. 9 is a partial cutaway perspective view of the anatomy of the throat with the laryngeal airway device of FIG. 1 positioned in the anatomy.
Figure 10:
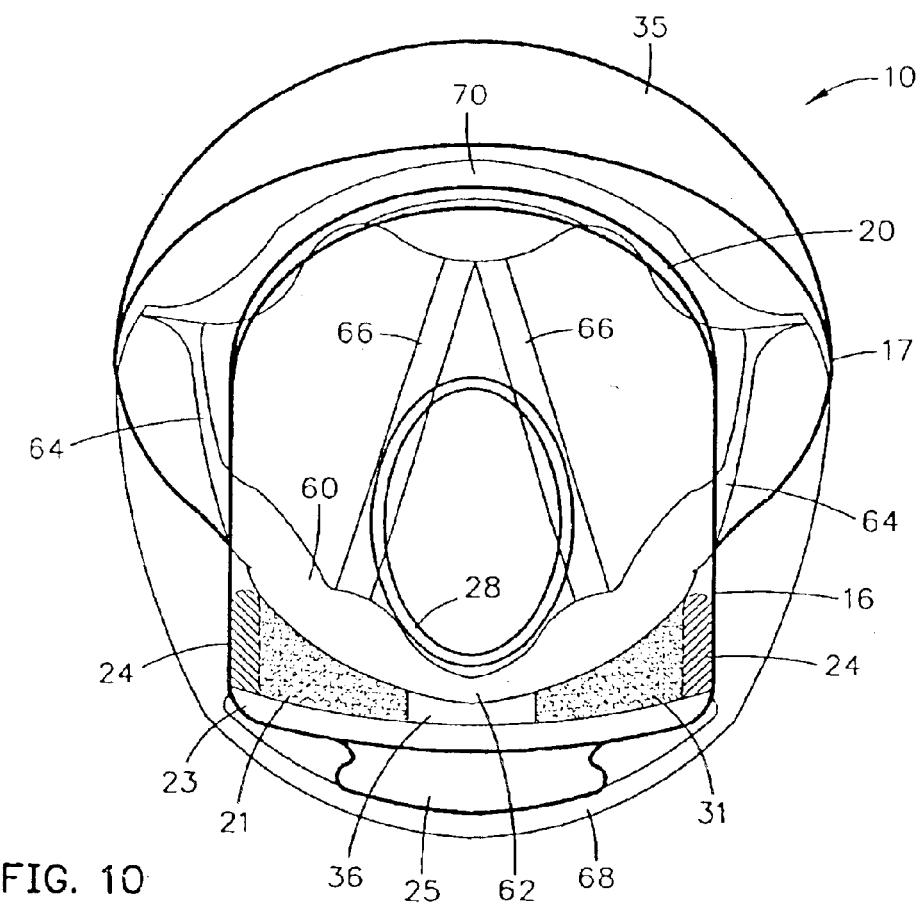
FIG. 10 is a schematic lateral cross-sectional representation of the anatomy of the throat taken along line B—B of FIG. 9.

FIG. 9 is a cutaway perspective view of the anatomy of a throat with the laryngeal airway device 10 seated against the laryngeal opening 60. FIG. 9 and FIG. 10 are provided for an explanation of how the laryngeal airway device is positioned and retained in the throat, although these functions of the device are not necessary to the practice of this invention.

FIG. 10 is a schematic lateral cross-sectional representation of the laryngeal anatomy taken along line B—B of FIG. 9. The direction of the view is toward the throat, from behind the sealing member 15. The view is schematic and imaginary, assuming that the sealing member is substantially transparent, with the outlines of its major components—the support member 16 and the compressible pad 17—indicated by heavy lines. In these views, the rim of the laryngeal opening is indicated by reference numeral 60, the inter arytenoid notch by reference numeral 62, the aryepiglottic folds by 64, the vocal chords by 66, the esophagus by 68, and the epiglottis by 70.

With respect to lateral positioning, the two opposing, substantially parallel lateral flanges 24 extend anteriorly and seat on each side of the cricoid cartilage which is disposed toward the bottom of the larynx, distal to the rim 60. When the cricoid cartilage is cradled between the lateral flanges 24, it is contained within the channel defined between the distal portions of by these elements, which assures lateral alignment of the tubular extension 28 within the laryngeal opening with respect to the vocal chords 66. FIGS. 1-3 illustrate the lateral flanges 24 as being located on the lateral edges 23 of the anterior supporting surface 21. In this illustration, the lateral flanges 24 extend for only part of the length of the sides; however, they may extend for shorter, or longer distances along the sides. In a side elevation view, the ridges may assume many shapes including, but not limited to, wall-like, rounded, square or rectangular, triangular, truncated triangular, or a combination of these shapes or any shapes that are equivalent and that serves the purpose of lateral retention. When viewed elevationally from the front of the support member 16, the lateral flanges 24 may have many shapes including, but not limited to, a wall, a tab, or a cylinder.

In considering cephalad-caudad positioning, refer to FIGS. 1, 3, 9, and 10. Recall the sigmoid shape of the anterior support surface 21, which is imposed on the anterior surface 31 of the compressible pad 17. The lower portion of the sigmoid that is described by the lower or distal portion 34 of the compressible pad is designed to seat between the larynx and the posterior pharynx, stabilizing the device 10. The lower portion of the support member 16, that is, the portion generally just above the distal end 22 to the end of the flange 25, is preferably angled posteriorly when molded. The posterior angle assures that the flange 25 and distal end 22 will be applied directly against the posterior wall of the pharynx when the airway 10 is advanced into its position of use. The midportion of the sigmoid shape is angled to abut the angled rim of the laryngeal opening 60, along the ary-epiglottic folds. The upper portion of the sigmoid shape is flattened to seal against the posterior side of the epiglottis, within the laryngeal opening. The "snout-like" tubular extension 28 protrudes through the hole 35, beyond the anterior surface 31, into the laryngeal opening 60. This snout helps create a fluid seal against the larynx by holding the laryngeal tissues out of the distal opening 28b, to prevent obstruction of air flow. As stated above, the tubular extension 28 can be shaped like a truncated cone, with its wide base attached to the distal end 14 of the air tube 12. The narrow distal end 28b is opened to allow air flow and it is this part that penetrates most deeply into the laryngeal opening 60.

Accurate cephalad-caudad depth placement is provided by the combination of the "snout-like" distal end 28b of the tubular extension 28 and the lower part 34 of the anterior surface 31 of the sealing member. This combination creates a "hook." The angle Φ (FIG. 3) between the distal end 28b of the tubular extension 28 and the lower anterior surface portion 34 is preferably an acute angle, greater than 0° and less than 90°. The base of the notch 62 formed between the arytenoid cartilages is made of the arytenoidous muscle overlaying the cricoid cartilage. These structures are very firm and assure a positive end-point when contacted with a longitudinal force. The hook described by the acute angle Φ is designed to catch on the cartilage and muscle between the arytenoid cartilages, on the posterior edge of the laryngeal opening. The hook described by the angle Φ engages over the posterior rim of the laryngeal opening, which is the obtuse angled edge of the rim. With the distal end 28b of the tubular extension 28 lodged inside the laryngeal opening, the hook cannot slip out distally or become displaced laterally when longitudinal pressure is applied to the airway. The arytenoid depression 36 and the anterior surface 31 assists in this positioning by receiving small corniculate tubercles that are on the posterior side of the larynx and that are near the arytenoid notch. The tubercles are received in the depression 36, and assist in positioning the laryngeal airway device 10 longitudinally in the laryngeal opening.

Referring once again to FIGS. 9 and 10, the cephalad-caudad positioning of the laryngeal airway device 10 may be understood. As shown in this figure, the inter arytenoid notch 62 is positioned between the tubular extension 28 and the distal portion 34 of the compressible pad 17. Although not shown in this view, the distal end 28b of the tubular extension 28 is located above the vocal chords 66. In addition, the arytenoid depression 36 has received the forward portion of the inter arytenoid notch 62 that includes the corniculate tubercles. This provides space in which the tubercles can be received, which enables the posterior side of the inter arytenoid notch to relax somewhat and move with the bottom portion of the tubular extension 28.

Retention of the Laryngeal Airway Device

In FIG. 3, there is shown an edge surface 88 on the proximal edge 33 of the compressible pad 17 and a surface 89 that extends from the proximal end 28a of the tubular extension 28 across the distal end 14 of the tube 12. The edge surface 88 and the tube surface 89 receive the tissues on the back portion of the tongue when the sealing member 15 has been advanced to seal against the laryngeal opening with lateral and depth positioning as described above. At this location, the back portion of the tongue relaxes, draping over the edge surface 88 of the proximal edge 33 and hanging down onto and around the surface 89. The rough texture of the surface of the tongue prevents the compressible material at the edge surface 88 from easily sliding across the surface of the tongue. This retains the airway in tight approximation with the larynx by anchoring it with the base of the tongue. The edge surface 88 that is presented by the structure of the distal portion of the laryngeal airway device 10 capitalizes on the flexibility of the tongue to capture the airway at the proximal edge 33 where the contact between the anchored base of the tongue and the edge surface 88 retains the edge 33 and prevents the airway 10 from being ejected from its correct positioning against the rim of the laryngeal opening.

Operation of the Introducer and Laryngeal Airway Device

The cooperative operations of the laryngeal airway device and the introducer will now be explained with reference to FIGS. 11-18.

Figure 11:
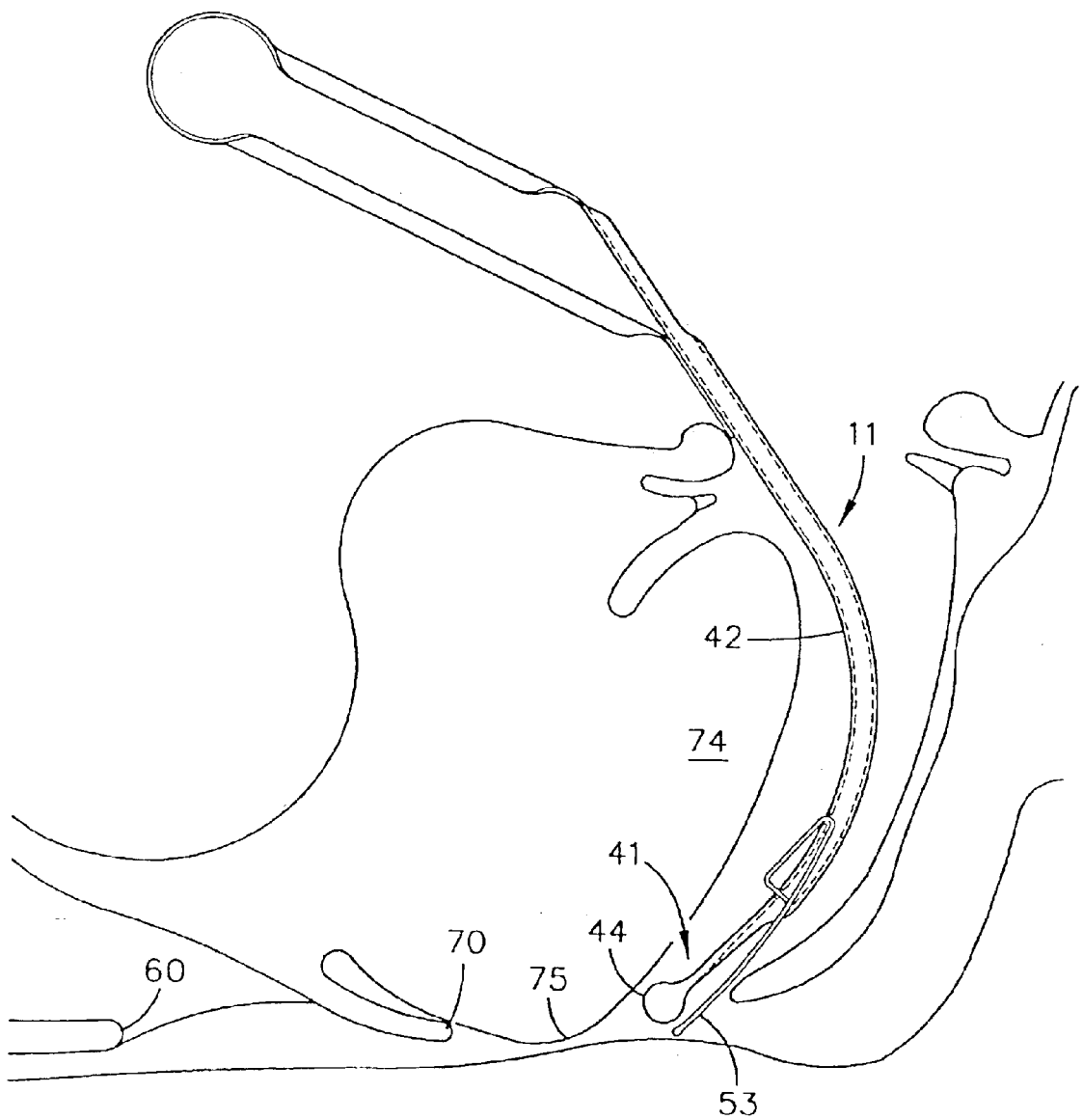
FIGS. 11-14 are schematic side cross-sectional representations of the anatomy of the throat showing the operation of the introducer of FIG. 4.
Figure 12:
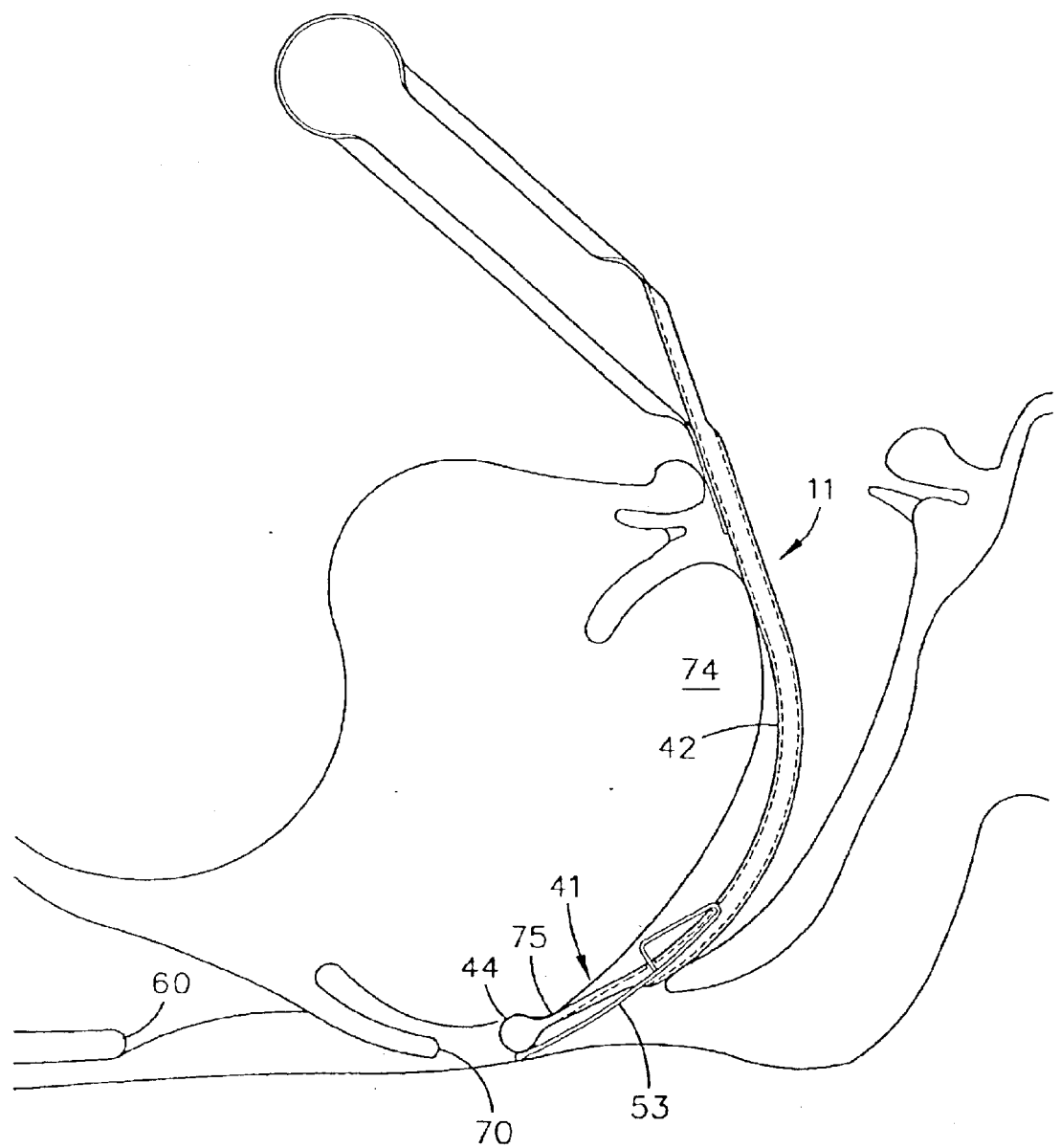
Figure 13:
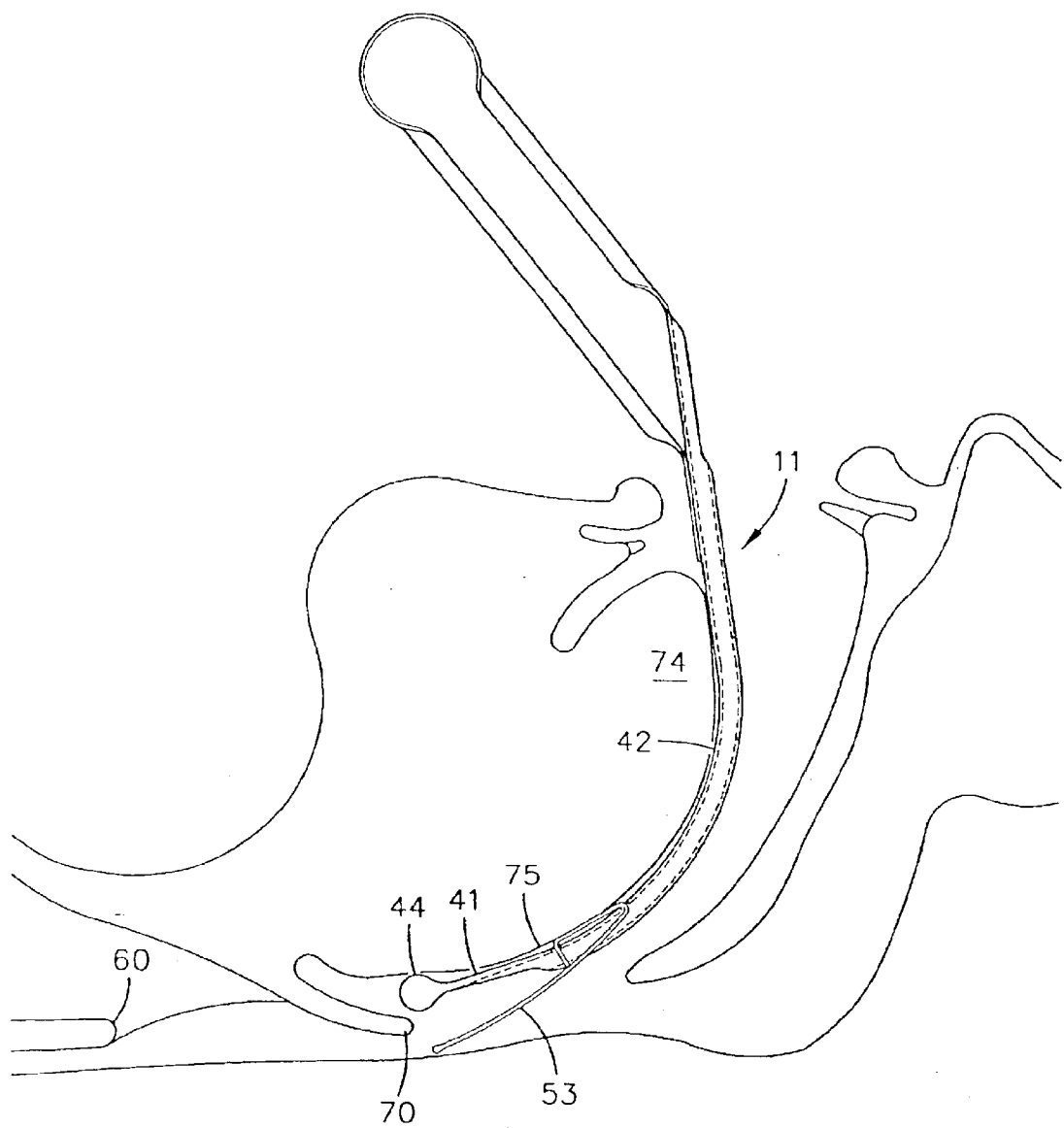
Figure 14:
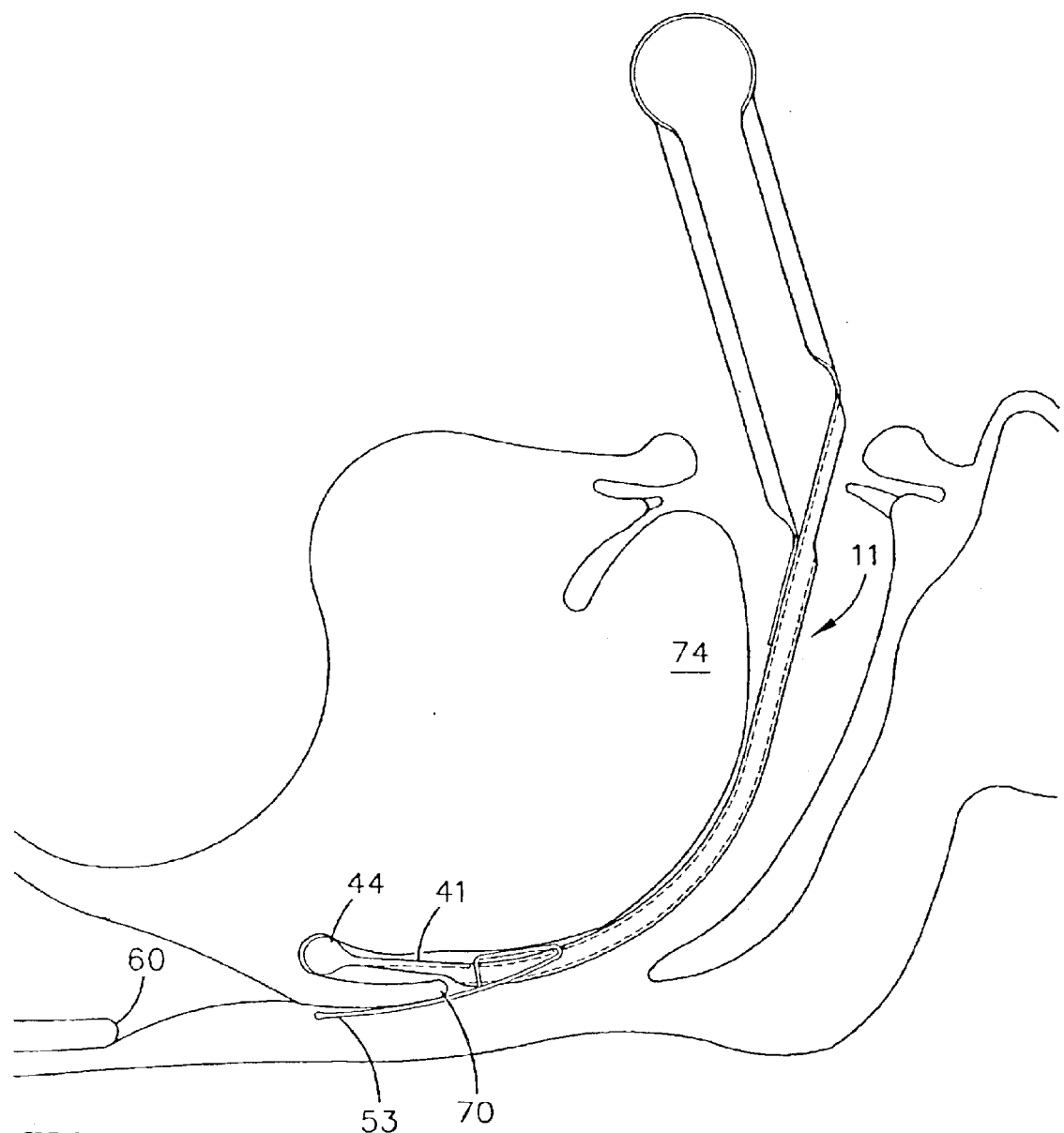
Figure 15:
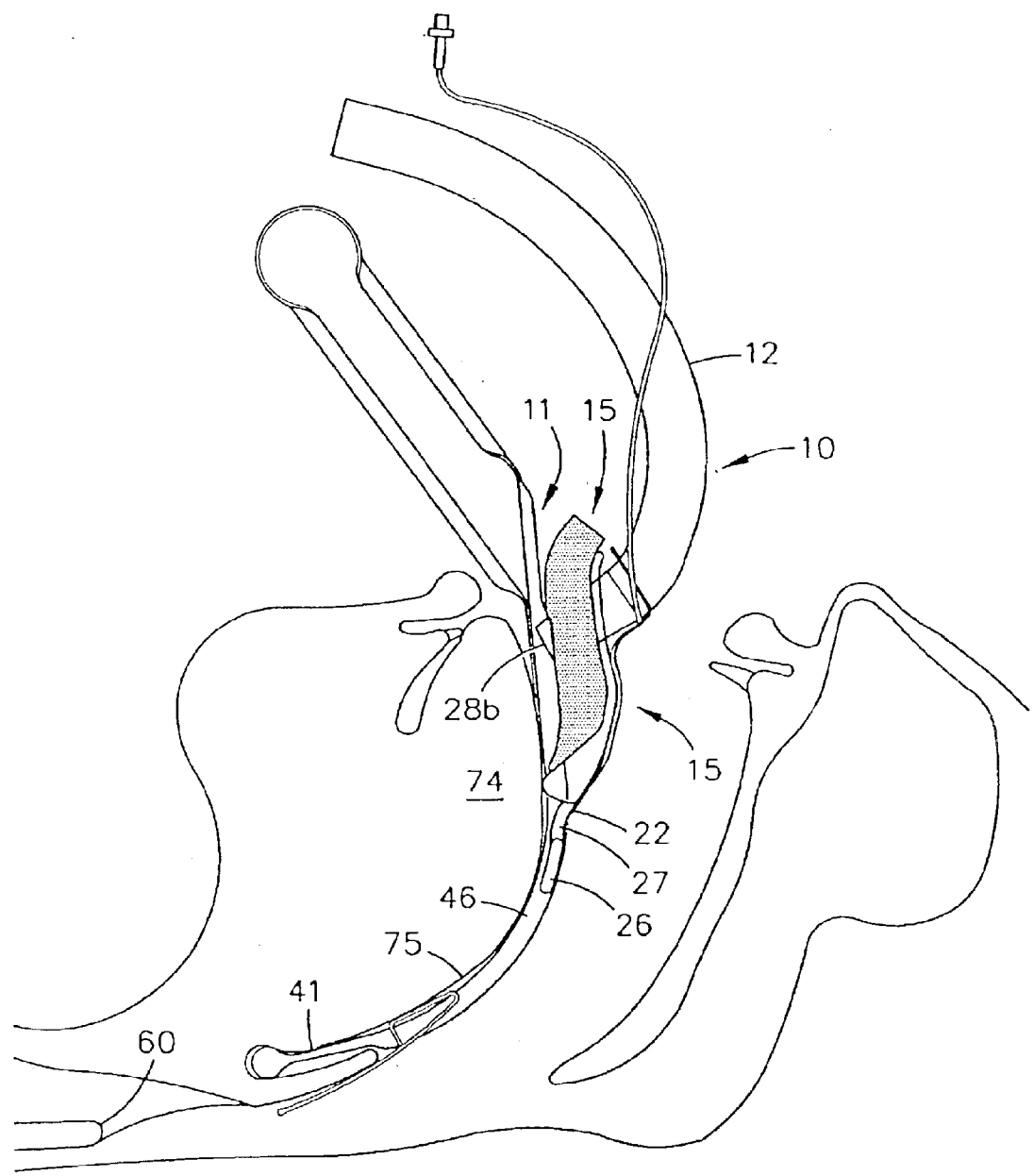
FIGS. 15-18 are schematic side cross-sectional representations of the anatomy of the throat showing the introduction and positioning of the laryngeal airway device of FIG. 1.
Figure 16:
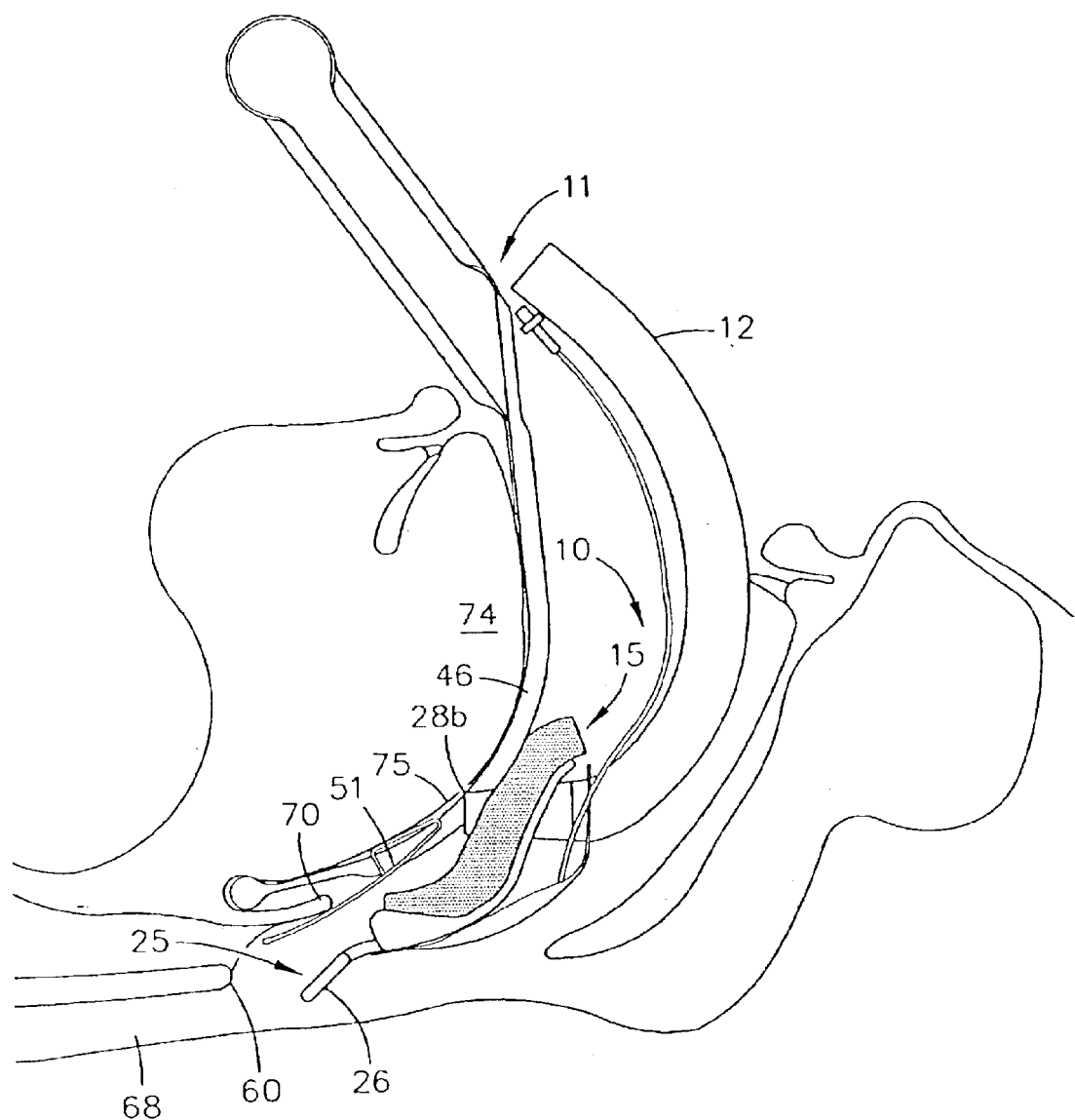
Figure 17:
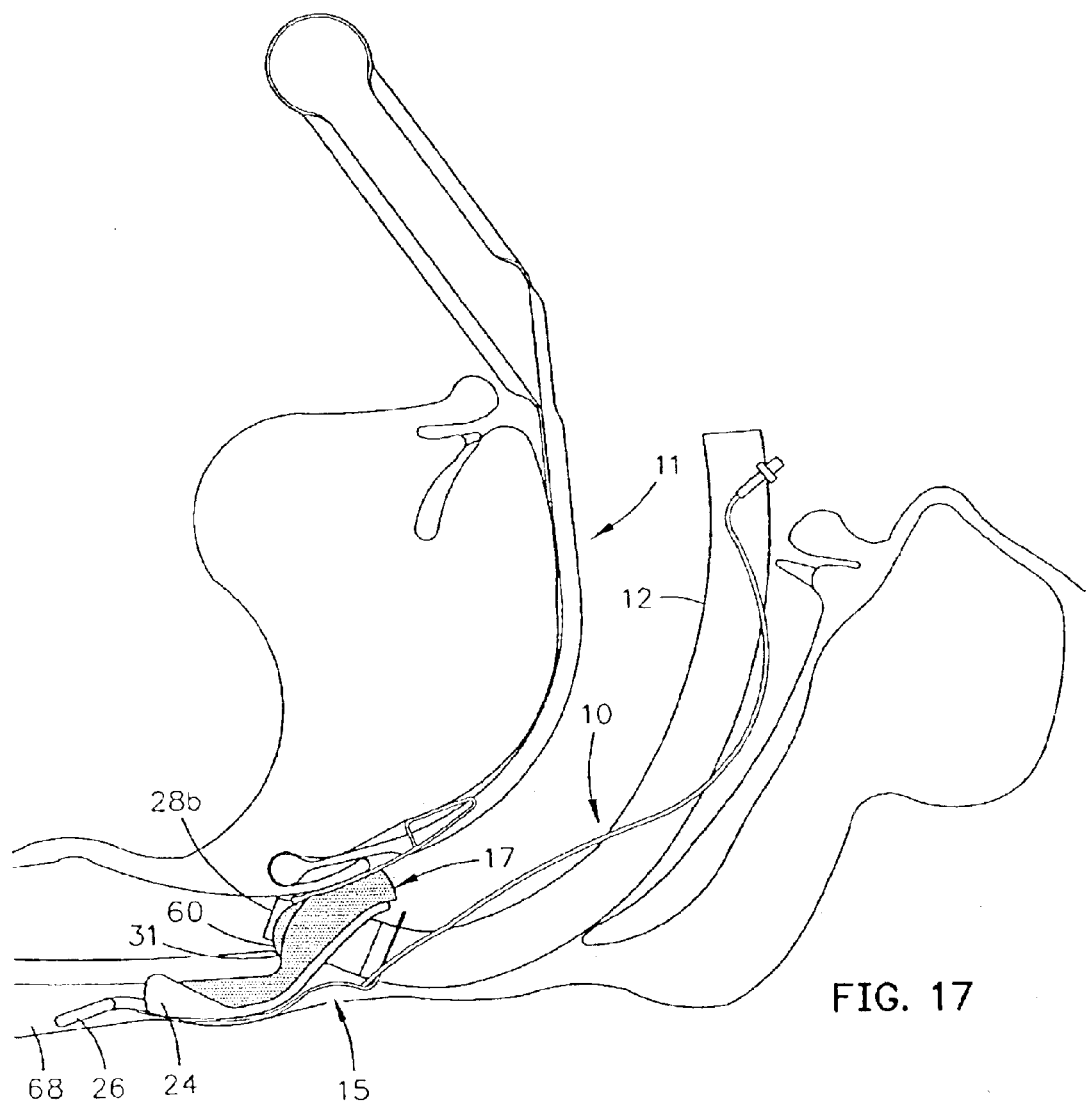
Figure 18:
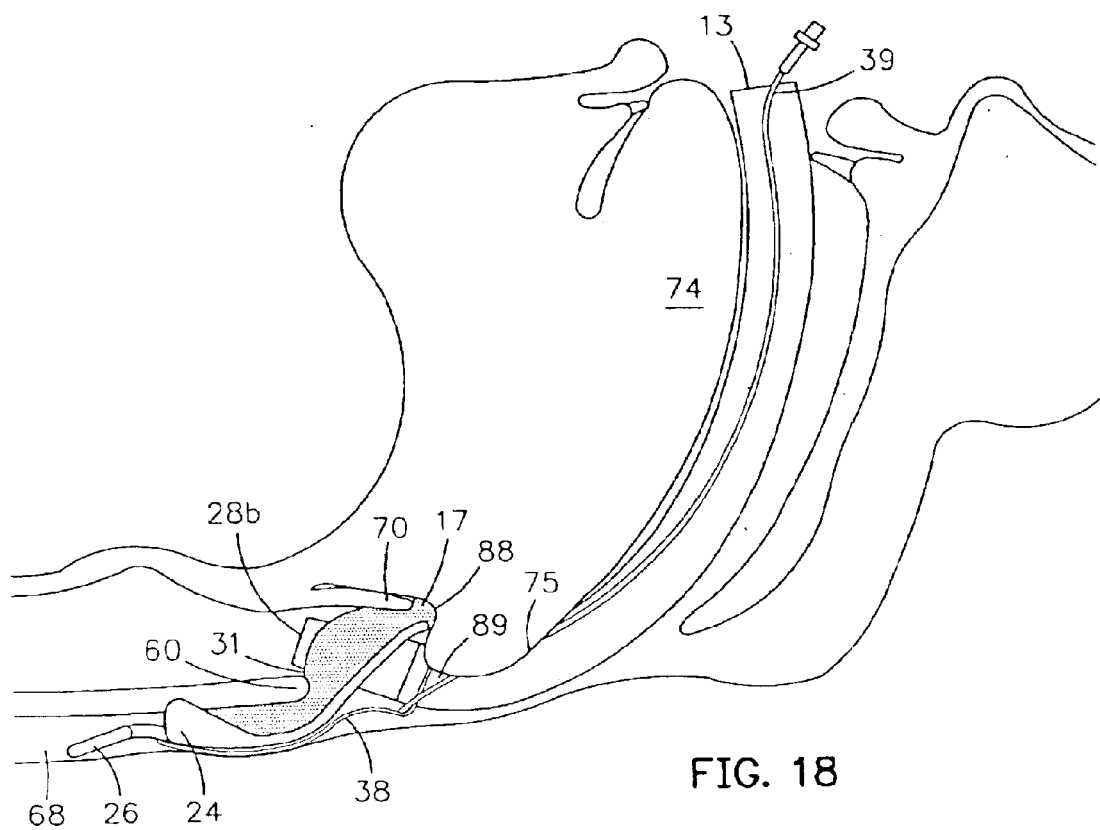

Initially, in FIG. 11, the introducer 11 is inserted, distal end 41 first, through the mouth, traversing the tongue 74 where, in FIG. 11, one of the rounded protuberances 44 is shown approaching the sharp curvature 75 at the back of the tongue. As the distal end of the introducer 11 advances, the flattened forward section 53 of the epiglottic engager 52 is rotated toward the posterior side near the distal end 41 by contacting the back of the throat. In FIG. 12, as the distal end 41 of the introducer 11 passes the sharp curve 75 at the back of the tongue 74, the narrow dimensions of the throat force the structure of the distal end 41 against the back of the tongue 74, lifting the lower tissues of the tongue away from the epiglottis 70. At this point, the flattened forward section 53 of the epiglottic engager 52 is fully rotated toward the distal end 41, between the rounded protuberances 44. In FIG. 13, the introducer 11 is pulled upwardly as it is advanced into the throat, further raising the tissue at the base of the tongue 74 and widening the throat, allowing the flattened forward section 53 of the epiglottic engager 52 to pivot away from the distal end 41 toward the back of the throat. As the distal end 41 of the introducer 11 is advanced to the position shown in FIG. 14, the epiglottis 70 is trapped between the distal end of the introducer 11 and the flattened forward section 53 of the epiglottic engager 52. This retains the tip of the epiglottis 70 upwardly, keeping it out of the space in the throat through which the sealing member of the laryngeal airway device must pass. At this point, the indentation 43 of the distal end 41 of the introducer has received the hyo-epiglottic ligament, while the protuberances 44 have been engaged under the hyoid bone to position the introducer 11. In FIG. 15, the laryngeal airway device 10 has been coupled to the introducer 11, with the tab 26 engaged in the track 46. The sealing member 15 is oriented as described above. The laryngeal airway device 10 is advanced along the introducer 11 over the tongue toward the curve 75 at the back of the tongue 74. In FIG. 16, the laryngeal airway device 10 has been advanced to the point where the flange 25 has emerged from the opening 51 at the distal end of the track 46. As the distal end of the laryngeal airway device 10 is advanced further into the throat, the flange 25 springs back to its first position with the tab 26 angled posteriorly toward the back of the throat. At this position, it can perform esophageal tracking. Referring to FIGS. 17 and 18, as the laryngeal airway device 10 is advanced further into the throat, it eventually seats against the rim 60 of the laryngeal inlet, with the distal end 28b of the tubular extension 28 extending within the laryngeal inlet and the anterior surface 31 of the compressible pad 17 engaging and sealing against the rim 60, and extending partly into the laryngeal opening in the vicinity of the distal end 28b. At the same time, the distal end of the sealing member 15 has tracked down the back of the throat with the tab 26 of the flange 25 tracking toward the esophagus 68. At this point, the above-described features of the laryngeal airway device have aligned and positioned it laterally and along the depth axis of the larynx. Now, the introducer 11 is withdrawn, leaving the laryngeal airway device 10 seated. Withdrawal of the introducer causes the tongue to drape down over the edge surface 88 and the surface 89 which retains the laryngeal airway device in the manner described above.

Clinical experience has shown that optimal lateral positioning with the laryngeal airway device 10 can be accomplished with a specific maneuver. Once the device 10 is positioned, with the flange 25 located between the larynx and the posterior wall in the pharynx in the upper reaches of the esophagus 68, the proximal end 13 of the laryngeal airway device 10 is grasped. The laryngeal airway device 10 is pulled very slightly out of the mouth against the tension of the tongue and then pushed back in. This maneuver is known as the "Arnold maneuver." The device 10 is not pulled so far out as to cause disengagement with the epiglottis 70 but merely to partially disengage the anterior surface 31 from the rim 60 of the laryngeal inlet. When the device 10 includes the distal end 28b, the Arnold maneuver disengages the tip of the distal end 28b from an arytenoid cartilage that may be obstructing the opening 60. On reinsertion, the distal end 28b is unobstructed and lies within the laryngeal inlet 60. The Arnold maneuver in conjunction with a device 10 that includes the lateral flanges 24 or their equivalent has been shown to dependably orient the device 10 in the lateral dimension with respect to the larynx. If the device 10 includes the snout like distal end 28b, the Arnold maneuver dependably places the distal end 28b within the laryngeal inlet 60 and clears tissue that may obstruct airflow.

If necessary to achieve a desired level of positive pressure, the seal that the laryngeal airway device makes with the laryngeal inlet may be assisted by inflation of the balloon 38 through the tube 39. This may follow the Arnold maneuver, if indicated. Inflation of the balloon 38 will rotate the sealing member anteriorly with respect to the laryngeal opening, further tensioning the opening and further urging the anterior surface of the compressible pad into sealing engagement against the opening.

Figure 19:
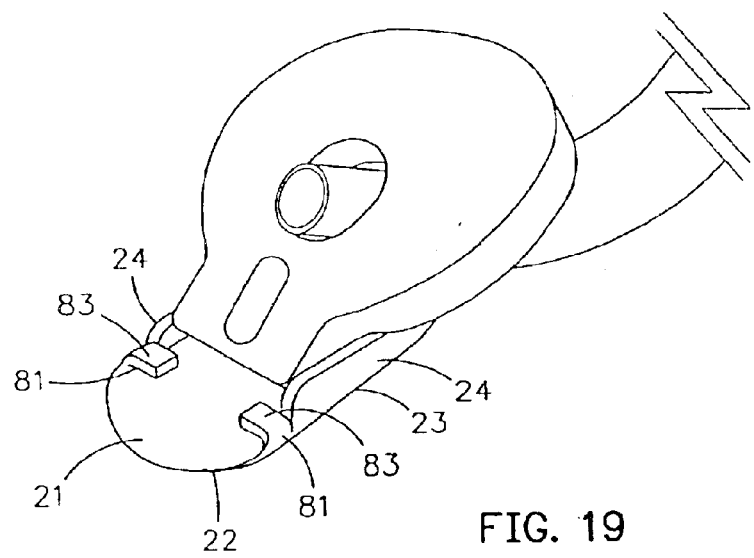
FIG. 19 depicts a portion of an alternate laryngeal airway device.
Figure 20:
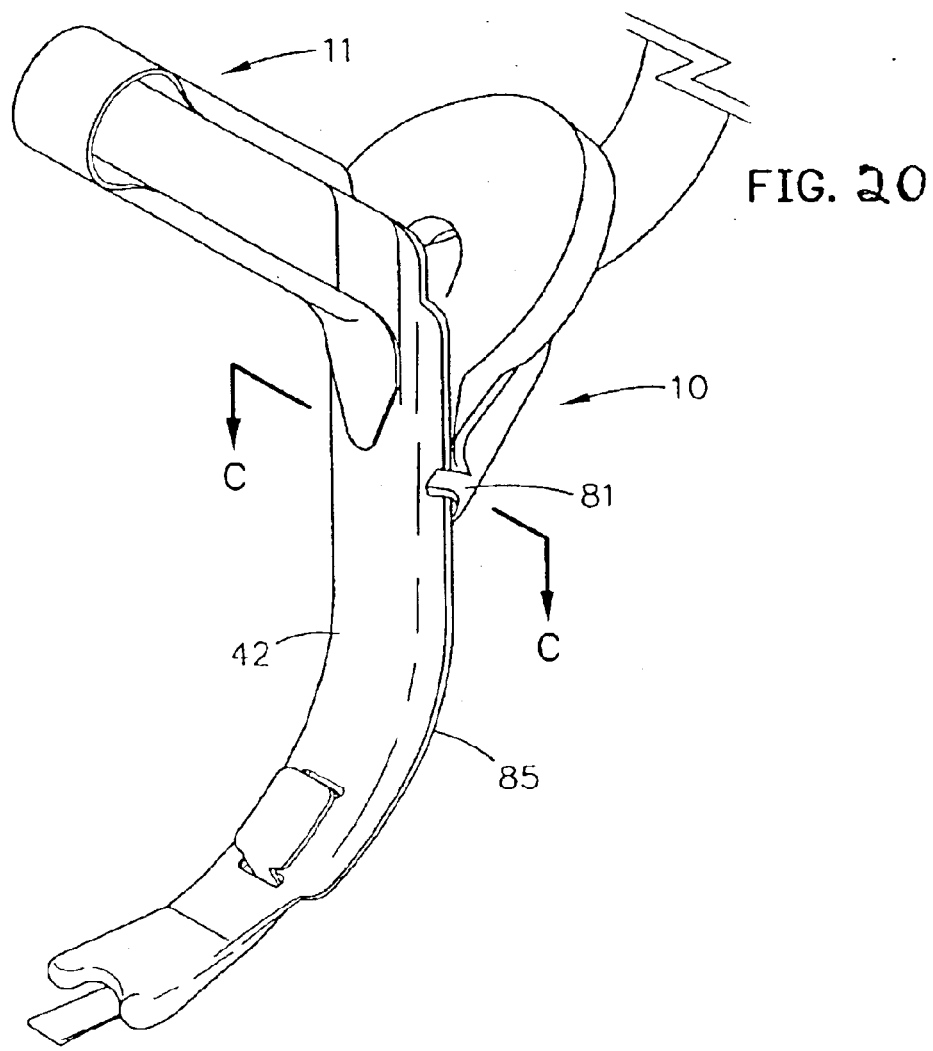
FIG. 20 illustrates the manner in which the laryngeal airway device of FIG. 19 is coupled to an introducer.
Figure 21:
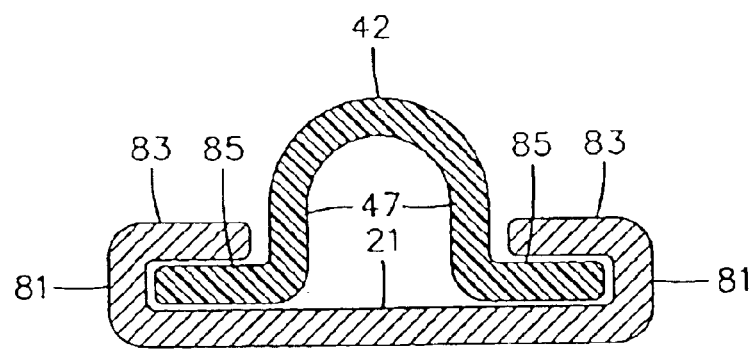
FIG. 21 is a sectional drawing taken along line C—C of FIG. 20.

The tracking or guiding feature of this invention may be implemented in many ways. FIGS. 19, 20, and 21 show an alternate embodiment of this feature. In this alternate embodiment, the coupler or rail-engagement mechanism on the sealing member of the laryngeal airway device includes a pair of opposing brackets on the distal portion of the sealing member, near the edges 23, between the lateral flanges 24 and the distal end 22. Each bracket includes a first wall portion 81 that rises from the anterior support surface 21 near an edge 23 of the support member 16, and a medially-extending portion 83 that is oriented toward the medially-extending portion of the opposing bracket. FIG. 20 is a rear perspective view of the laryngeal airway device coupled to the introducer 11. FIG. 21 shows a front cross-sectional view of the introducer 11 with the distal portion of the laryngeal airway device 10 coupled to it; this view is along line C—C of FIG. 20. In this embodiment, the introducer 11 is identical in most respects with the embodiment of the introducer illustrated in FIGS. 4-7. The exception is in the structure of the track in the embodiment illustrated in FIG. 20. The track of the introducer 11 in FIG. 20 includes two opposing slide rails that are formed by upwardly extending wall portions 47, which transition to outwardly-extending sections 85. The outwardly-extending sections 85 of the track engage the medially-extending portions 83 of the opposing brackets, permitting the laryngeal airway device to engage and slidably move along the track from the proximal to the distal end of the introducer 11. At the distal end of the introducer, the widths of the outwardly-extending portions 85 reduce medially until only the upward extensions 47 remain, thereby permitting the laryngeal airway device to disengage from the introducer 11.

Many variations of the coupler/track combination are possible. Not all are included in the embodiments that have been illustrated and described. Possible alternate embodiments could include a track with a single rail on the posterior side of the introducer and a coupler on the sealing member that is adapted to engage it.

Alternate Embodiment

Figure 22:
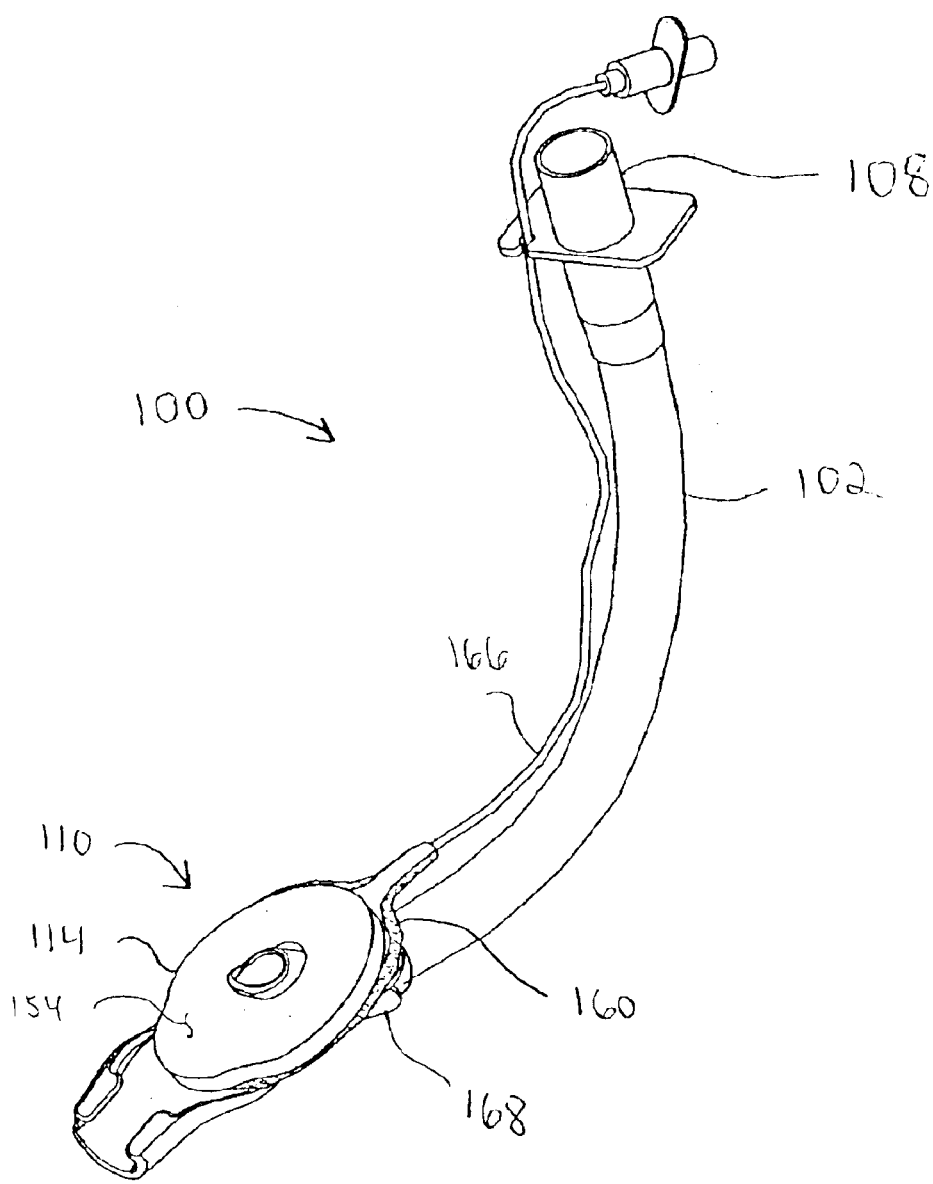
FIG. 22 is a perspective view of a laryngeal airway device configured in accordance with the present invention.
Figure 23:
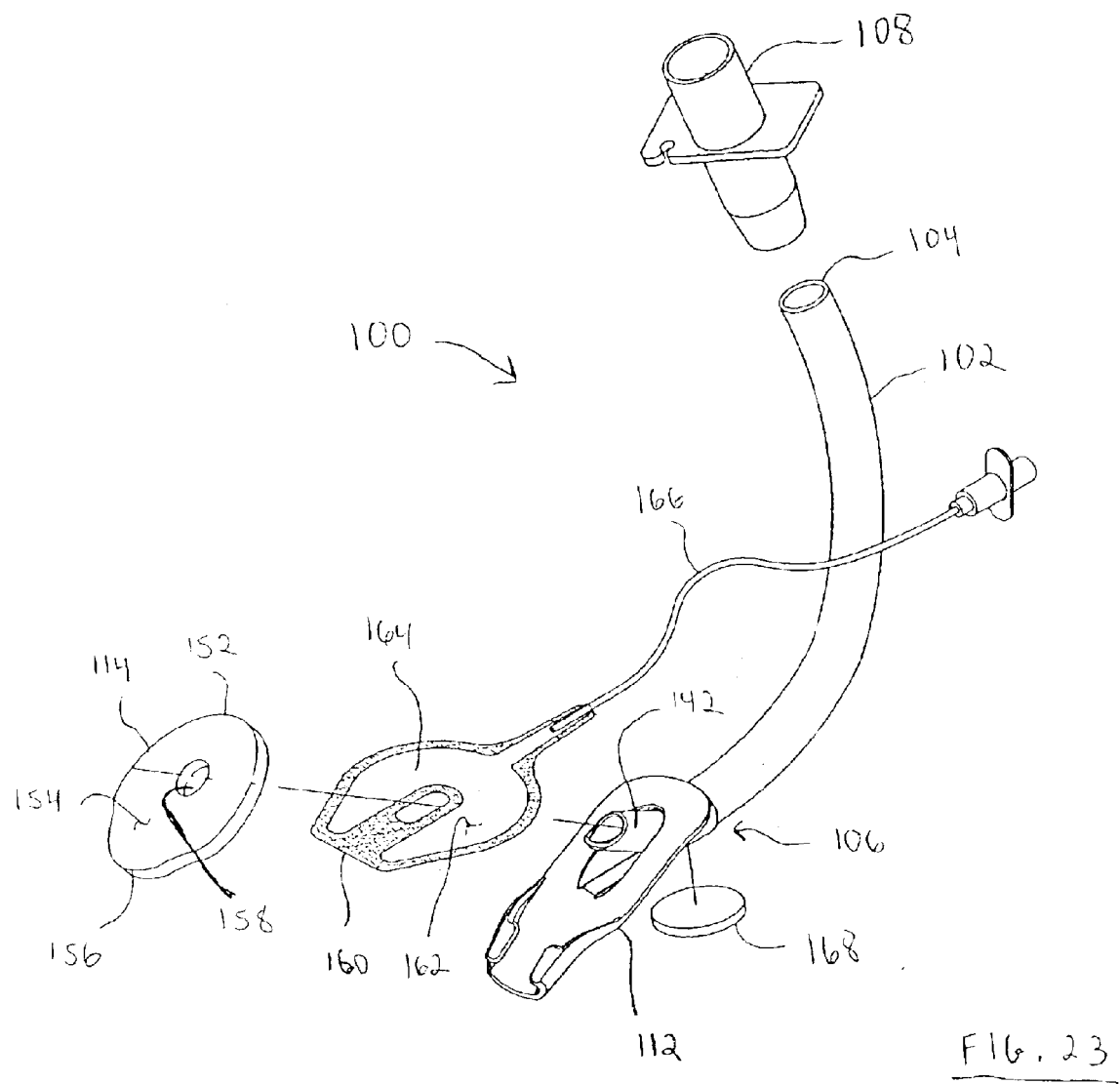
FIG. 23 is an exploded view of the laryngeal airway device of FIG. 22.
Figure 28:
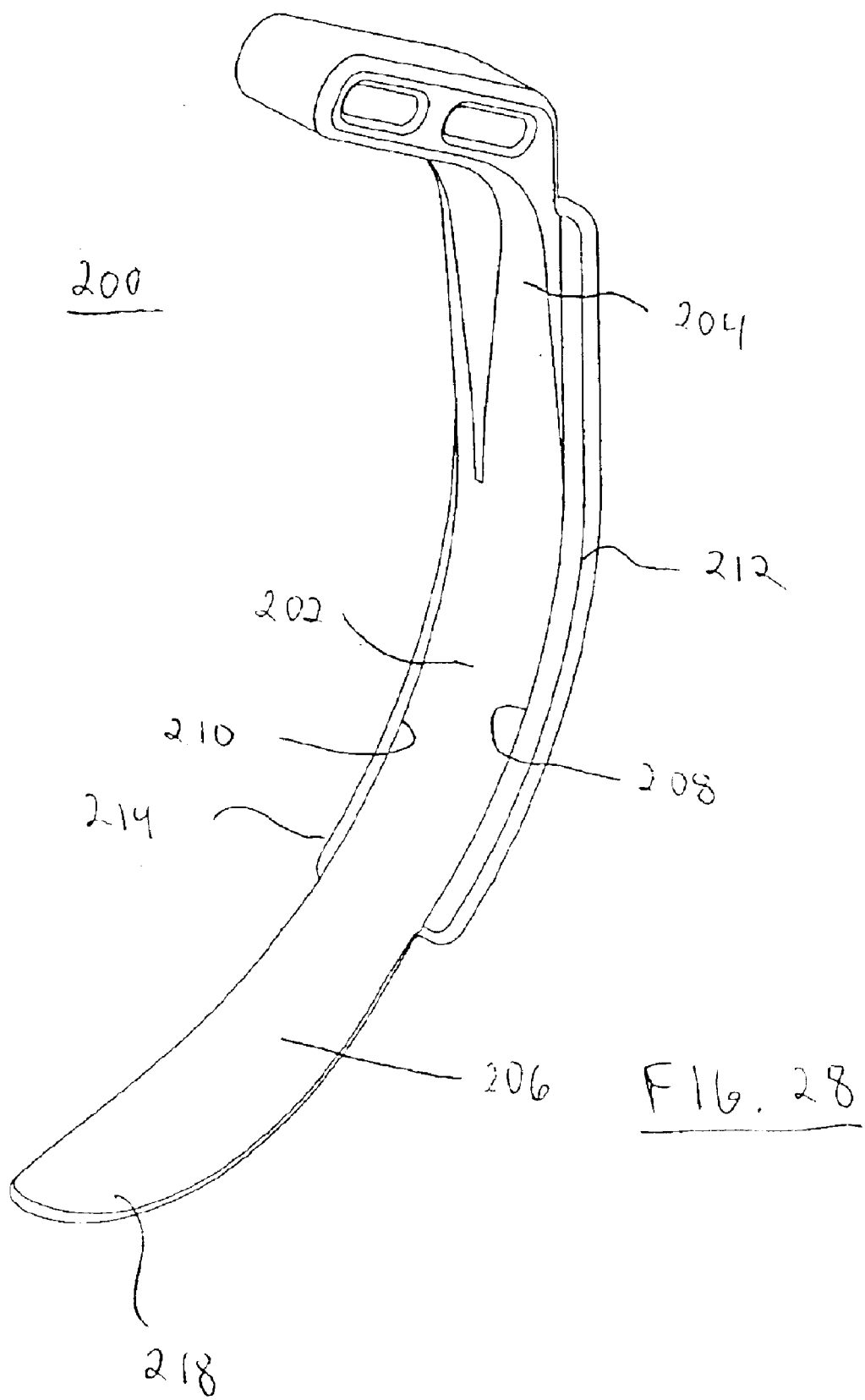
FIG. 28 is a perspective view of an introducer suitable for use with the laryngeal airway device of FIG. 22.

FIG. 22 is a perspective view of a laryngeal airway device 100 configured in accordance with the present invention, and FIG. 23 is an exploded view of laryngeal airway device 100. Device 100 shares a number of features with the other laryngeal airway devices described above. Accordingly, for the sake of brevity, the description of such common features may not be repeated in the context of device 100. Briefly, the sealing member of device 100 includes several features not found in the previously described embodiments.

Laryngeal airway device 100 includes a flexible air tube 102 having first (proximal) and second (distal) ends 104 and 106, respectively. The interior of air tube 102 defines an airway. The air tube 102 has a curved shape that conforms to the contour of the back of the tongue. A connector 108 is attached to the proximal end 104 to connect the air tube 102 to a ventilating means, which is not shown. A sealing member 110 is attached to the air tube 102 near its distal end 106. The sealing member 110 includes a support member 112 and a compressible foam pad 114.

FIGS. 24-26 illustrate support member 112 in detail. Support member 112 has an upper (proximal) edge 116, an anterior support surface 118, a distal end 120, and sides 122/124. Support member 112 includes a coupler (for coupling to an introducer) near distal end 120; in the example embodiment, the coupler includes a first tab 126 elevated above anterior support surface 118, a second tab 128 elevated above anterior support surface 118, and a track 130 defined at least in part by tabs 126/128 and a portion of anterior support surface 118. First tab 126 is supported by a first flange or sidewall 132 located between first tab 126 and anterior support surface 118, and second tab 128 is supported by a similarly configured second flange or sidewall 134. Track 130 is further defined by sidewalls 132/134, which are approximately parallel in the region under tabs 126/128. Thus, track 130 is suitably formed near distal end 120 of support member 112 to provide a coupler for sealing member 110.

The coupler of support member 112 may be configured as described above in connection with FIGS. 19-21. In this regard, tabs 126/128, along with sidewalls 132/134 form two opposing brackets. Tabs 126/128 form the medially-extending portions of the respective brackets, while sidewalls 132/134 form the wall portions of the respective brackets.

In the preferred embodiment, sidewall 132 extends beyond tab 126, and sidewall 134 extends beyond tab 128, toward the proximal end of sealing member 110 (and toward the proximal end of support member 112). In this regard, sidewalls 132/134 can also function as a pair of opposing cricoid retainers 136/138, that rise upwardly along the respective sides 122/124 from the distal portion of the anterior support surface 118. As best shown in FIG. 26, sidewalls 132/134 can be tapered from a height corresponding to tabs 126/128 down to anterior support surface 118. Such tapering enables support member 112 to flex near its midpoint above sidewalls 132/134. Cricoid retainers 136/138 may be configured as described above in connection with lateral flanges 24 (see FIG. 2).

Support member 112 is configured for coupling to air tube 102 via an inlet 140. Inlet 140 communicates with a tubular extension or snout 142, which further defines the airway associated with air tube 102. Tubular extension 142 is configured such that it protrudes beyond anterior support surface 118. Tubular extension 142 includes a body section 144 having a longitudinal axis, a lower section 146 facing anterior support surface 118, an upper section 148 opposite lower section 146, and a cupped lip 150. Cupped lip 150 is formed as a result of the partially tubular characteristic of the end of tubular extension 142, which resembles an inverted hood.

As best shown in FIG. 26, cupped lip 150 is formed such that lower section 146 of tubular extension 142 protrudes farther toward distal end 120 of support member 112 than does the upper section 148 of tubular extension 142. In this regard, lower section 146 terminates at cupped lip 150. As shown in FIG. 26, the outer surface of cupped lip 150 curves inward toward the central longitudinal axis of tubular extension 142. The outer shape of cupped lip 150 resembles a portion of a sphere or dome. Thus, the end of tubular extension 142 resembles the bottom of a thick-walled test tube with a portion removed. The rounded/spherical outer shape of cupped lip 150 is best shown in FIG. 24 and FIG. 26. From the side view perspective of FIG. 26, cupped lip 150 has a curved profile (in contrast to a straight angled profile) that spans from the apex point of upper section 148 to the termination point of lower section 146. Consequently, cupped lip 150 includes a nonplanar rim. As shown in FIG. 26, the rim of cupped lip 150 is shaped such that it can cradle an appropriately sized cylindrical object. Indeed, the profile of cupped lip 150 shown in FIG. 26 may represent an arc of a circle. As shown in FIG. 26, the shape and configuration of cupped lip 150 forms an opening that faces anteriorly, in contrast to an opening that is perpendicular to the longitudinal axis of tubular extension 142. As best shown in FIG. 25, the cupped lip 150 is configured such that the tip of tubular extension 142 is beveled or tapered (in contrast to an embodiment where the end of tubular extension 142 represents a straight cut perpendicular to its longitudinal axis). The curvature of the outer surface of cupped lip 150 provides a smooth taper and transition from the "point" of cupped lip 150 (identified by reference number 151 in FIG. 25) to the outer width of body section 144.

The beveled snout with anteriorly facing opening facilitates avoidance of protruding cuneiform and corniculate tubercles or oversized arytenoid cartilages when in use. The cupped lip 150 tends to deflect the more problematic posterior structure of the laryngeal inlet (arytenoid and cuneiform cartilages), while the bevel tapers the snout such that it becomes self-centering within the laryngeal vestibule. In particular, the beveled, tapered snout tends to gravitate toward the inter arytenoid notch, which lies at the midline of the laryngeal inlet posteriorly. This self-centering feature improves the likelihood of proper delivery of the tubular extension 142 into the laryngeal vestibule on initial placement and during subsequent manipulation, when required. An added advantage of the beveled snout design is the reduction in the space occupied by the snout, relative to non-beveled designs. The reduced bulk makes it easier to fully seat the device upon the initial insertion, thereby reducing the likelihood of subsequent manipulation or repeated insertion attempts. FIG. 27 is a schematic side cross-sectional representation of the anatomy of the throat showing the introduction of the laryngeal airway device of FIG. 22. FIG. 27 illustrates how cupped lip 150 is positioned relative to the anatomy of the throat.

Referring again to FIGS. 22 and 23, the compressible pad 114 preferably has a pear-like shape with an upper, or proximal portion 152, an anterior surface 154, a lower or distal portion 156, and a posterior surface (hidden from view) opposite anterior surface 154. The upper portion 152 is relatively wider than the lower portion 156. The compressible pad 114 includes a hole 158 formed therein that is positioned on a longitudinal midline of the pad 114. The hole 158 opens through the anterior surface 154 and extends through the pad 114, aligned longitudinally with the tubular extension 142 of support member 112. As shown in FIG. 22, tubular extension 142 is disposed in the hole 158. The length of the compressible pad 114 that extends from tip to tip is such that, when the pad 114 is joined to the support member 112, the distal end of the pad 114 is positioned between the sidewalls 136/138 (see FIG. 25), set back from the distal end of the pad 114. This leaves open a channel defined laterally between distal portions of the sidewalls 136/138 and longitudinally between the distal end of the compressible pad 114 and the distal end of the support member 112.

As is best seen in FIG. 23, an inflatable balloon 160 is positioned between the anterior support surface 118 of support member 112 and the compressible pad 114. Balloon 160 includes an anterior surface 162, a posterior surface (hidden from view) opposite anterior surface 162, and a donut-shaped or horseshoe-shaped air chamber 164. In the preferred embodiment, the posterior surface of balloon 160 is attached to the anterior support surface 118 of support member 112, and the anterior surface 162 of balloon 160 is attached to the posterior surface of the compressible pad 114. Air chamber 164 is configured such that it partially surrounds tubular extension 142. Specifically, air chamber 164 is positioned such that the horseshoe shape opens toward the distal end of sealing member 110. A small tube 166 is provided for inflating the balloon 160. The balloon 160 maybe provided to compensate for unusual variations in airway anatomy. It will not be necessary to inflate the balloon 160 in all patients in order to effect an airway seal. When deflated, balloon 160 is thin and flat such that compressible pad 114 is primarily supported by support member 112. When inflated, however, balloon 160 raises the posterior surface of compressible pad 114 above the anterior support surface 118 of the support member 112. In this manner, compressible pad 114 is supported at least in part by balloon 160. The configuration of balloon 160, e.g., the horseshoe shape of balloon 160, causes the proximal portion 152 of pad 114 to lift more than the distal portion 156 of pad 114.

The location of inflatable balloon 160 between compressible pad 114 and support member 112 promotes concentration of the inflation in the sealing area of pad 114. This configuration also reduces the likelihood that balloon 160 will be caught on the patient's teeth during insertion.

Laryngeal airway device 100 may also include a posterior cushion 168 attached to sealing member 110. In the example embodiment, cushion 168 is attached to the back of inlet 140, near the point where inlet 140 joins air tube 102. Cushion 168 is suitably configured to disperse the pressure exerted by the airway device 100 against the posterior wall of the pharynx (see FIG. 27, which illustrates the relative positioning of cushion 168 within the throat). Cushion 168 may also be attached to device 100 such that it masks the joint between inlet 140 and air tube 102. In a practical embodiment, cushion 168 is a foam pad that is affixed to support member 112 using a suitable adhesive or glue. Cushion 168 may include creases, running parallel to the longitudinal direction of air tube 102, to facilitate better adhesion to support member 112.

Figures 29, 30:
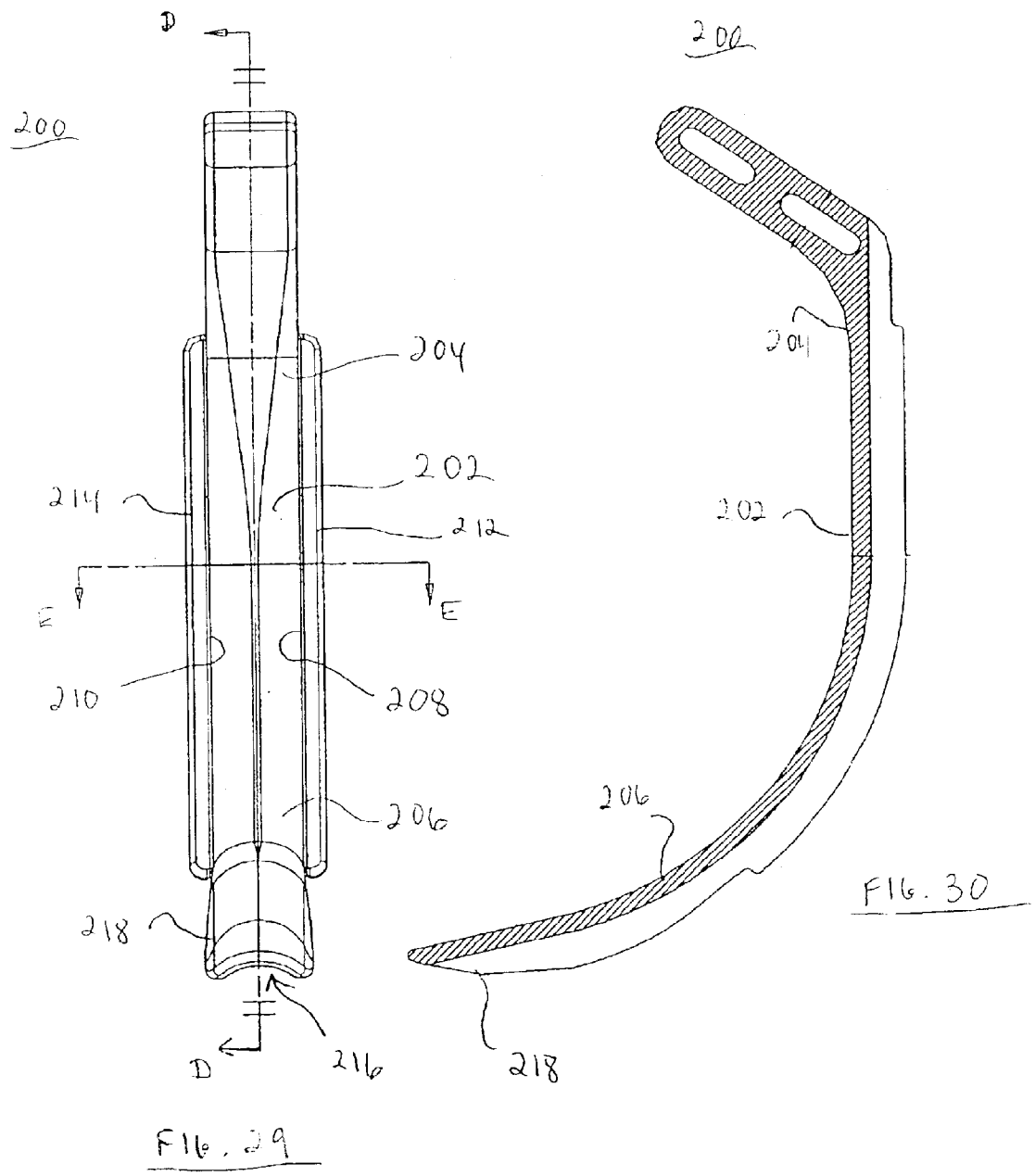
FIG. 29 is a front elevation view of the introducer of FIG. 28.
FIG. 30 is a cross-sectional view of the introducer taken along line D—D of FIG. 29.

Refer now to FIGS. 28-31, which illustrate one embodiment of an introducer 200 with which laryngeal airway device 100 is used. The introducer 200 is a relatively stiff plastic or metal blade-like device having a straight portion and a curved portion. Preferably, though not necessarily, the shape may be that of a capital "J." Introducer 200 includes an inner blade 202 having a proximal end 204, a distal end 206, and opposing longitudinal edges 208/210. Introducer 200 also includes a first slide rail 212 connected to first longitudinal edge 208 and a second slide rail 214 connected to second longitudinal edge 210. In this respect, introducer 200 may be configured as described above in connection with FIGS. 19-21. In practical embodiments, slide rails 212/214 may be integrally formed with inner blade 202. Slide rails 212/214 each extend from near the proximal end 204 of inner blade 202 to near the distal end 206 of inner blade 202. As best shown in FIG. 29, slide rails 212/214 form thin "wings" that protrude from the sides of inner blade 202. In the example embodiment, the outer edges of slide rails 212/214 are parallel. Slide rails 212/214 are configured such that the coupler of the support member 112 slidably engages the rails.

Figure 31:
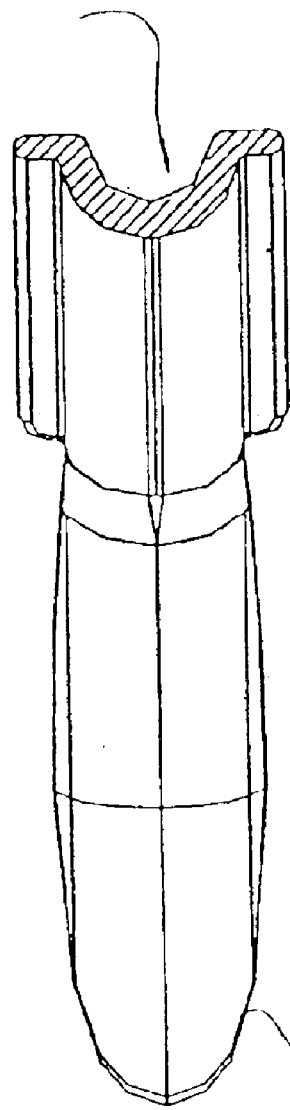
FIG. 31 is a cross-sectional view of the introducer taken along line E—E of FIG. 29.

As best shown in FIG. 31, inner blade 202 is curved when viewed from a lateral cross section. This curvature of inner blade 202 forms a guide trough 216 defined by the posterior side of inner blade 202. Although not shown in FIG. 31, the guide trough 216 extends from near the proximal end 204 of inner blade 202 to the distal end 206 of inner blade 202, and through a blade tip 218 of introducer 200. FIG. 29 shows trough 216 exiting at the distal end of blade tip 218. Blade tip 218, which may be connected to or near the distal end of inner blade 202 (or integrally formed with inner blade 202), also has a laterally curved shape that defines guide trough 216. The laterally curved shape of blade tip 218 has an apex at the anterior side of blade tip 218, as depicted in FIG. 29. Guide trough 216 is suitably configured to accommodate the snout of airway device 100 during insertion into the person's throat.

The coupling of airway device 100 to introducer 200 is similar to that depicted in FIG. 19 and FIG. 20. The insertion of airway device 100 into the throat of a patient is accomplished using a technique similar to that depicted in FIGS. 11-18. First, introducer 200 is positioned into the throat and manipulated as described above. Next, airway device 100 is coupled to introducer 200 and advanced into the throat. Eventually, the coupler on airway device 100 will be advanced beyond the ends of slide rails 212/214, thus releasing airway device 100 from introducer 200. The introducer 200 can then be removed to allow adjustment of airway device 100 and inflation of balloon 160 if necessary.

Clearly, many other embodiments and modifications of this invention will occur readily to those of ordinary skill in the art in view of these teachings. Therefore, this invention is to be limited only by following claims, which include all such embodiments and modifications when viewed in conjunction with the above specification and accompanying drawings.

What is claimed is:

1. A laryngeal airway device comprising:
   an air tube having a first end and a second end, said air tube defining an airway; and
   a sealing member mounted to said air tube proximate said first end, said sealing member comprising:
      a support member having an anterior support surface; and
      a tubular extension protruding beyond said anterior support surface, said tubular extension further defining said airway, said tubular extension terminating at a cupped lip.

2. A laryngeal airway device according to claim 1, wherein:
   said support member has a proximal end and an opposing distal end;
   said tubular extension comprises a body having a longitudinal axis, a lower section facing said anterior support surface, and an upper section opposite said lower section; and said lower section protrudes farther than said upper section toward said distal end of said support member.

3. A laryngeal airway device according to claim 2, wherein said lower section terminates at said cupped lip.

4. A laryngeal airway device according to claim 1, wherein said cupped lip includes an outer surface that curves inward toward said airway.

5. A laryngeal airway device according to claim 1, wherein said cupped lip has a curved profile.

6. A laryngeal airway device according to claim 1, wherein said cupped lip includes a nonplanar rim.

7. A laryngeal airway device according to claim 1, wherein said cupped lip is configuredto promote self-centering of said laryngeal airway device within the laryngeal vestibule.

8. A laryngeal airway device comprising:
an air tube having a first end and a second end; and
a sealing member mounted to said air tube proximate said first end, said sealing member comprising:
a support member having an anterior support surface;
a compressible pad; and
an inflatable balloon positioned between said anterior support surface and said compressible pad.

9. A laryngeal airway device according to claim 8, wherein:
said inflatable balloon comprises an anterior surface and a posterior surface;
said compressible pad comprises an anterior surface and a posterior surface;
said posterior surface of said inflatable balloon is attached to said anterior support surface; and
said anterior surface of said inflatable balloon is attached to said posterior surface of said compressible pad.

10. A laryngeal airway device according to claim 9, wherein:
when deflated, said inflatable balloon is flat; and
when inflated, said inflatable balloon raises said posterior surface of said compressible pad above said anterior support surface.

11. A laryngeal airway device according to claim 8, further comprising a tubular extension protruding beyond said anterior support surface, said tubular extension communicating with said air tube, wherein said inflatable balloon includes a horseshoe-shaped air chamber that partially surrounds said tubular extension.

12. A laryngeal airway device comprising:
an air tube having a first end and a second end;
a sealing member mounted to said air tube proximate said first end, said sealing member comprising an anterior support surface and a distal end; and
a coupler on the sealing member near said distal end, said coupler comprising:
a first tab elevated above said anterior support surface;
a second tab elevated above said anterior support surface; and
a track defined at least in part by said first tab, said second tab, and a portion of said anterior support surface.

13. A laryngeal airway device according to claim 12, wherein said coupler further comprises:
a first sidewall between said first tab and said anterior support surface, said first sidewall supporting said first tab above said anterior support surface; and
a second sidewall between said second tab and said anterior support surface, said second sidewall supporting said second tab above said anterior support surface.

14. A laryngeal airway device according to claim 13, wherein said track is further defined by said first and second sidewalls.

15. A laryngeal airway device according to claim 13, wherein:
said sealing member includes a proximal end opposite said distal end;
said first sidewall extends beyond said first tab toward said proximal end of said sealing member; and
said second sidewall extends beyond said second tab toward said proximal end of said sealing member.

16. A laryngeal airway device according to claim 15, wherein:
said first sidewall is tapered from a height corresponding to said first tab to said anterior support surface; and
said second sidewall is tapered from a height corresponding to said second tab to said anterior support surface.

17. A laryngeal airway kit comprising;
a laryngeal airway device comprising:
an air tube having a first end and a second end;
a sealing member mounted to said air tube proximate said first end, said sealing member comprising an anterior support surface and a distal end; and
a coupler on the sealing member near said distal end, said coupler comprising a first tab elevated above said anterior support surface, a second tab elevated above said anterior support surface, and a retention channel defined at least in part by said first tab, said second tab, and a portion of said anterior support surface; and
an introducer comprising:
an inner blade having a proximal end, a distal end, a first longitudinal edge and a second longitudinal edge;
a first slide rail connected to said first longitudinal edge, said first slide rail extending from near said proximal end to near said distal end;
a second slide rail connected to said second longitudinal edge, said second slide rail extending from near said proximal end to near said distal end;
wherein said first tab, said second tab, said first slide rail, and said second slide rail are configured such that said coupler slidably engages said first and second slide rails.

18. A laryngeal airway kit according to claim 17, wherein said coupler further comprises:
a first sidewall between said first tab and said anterior support surface, said first sidewall supporting said first tab above said anterior support surface; and
a second sidewall between said second tab and said anterior support surface, said second sidewall supporting said second tab above said anterior support surface;
wherein the distance between said first and second sidewalls is greater than the widest point between said first and second slide rails.

19. A laryngeal airway kit according to claim 18, wherein said track is further defined between said first and second sidewalls.

20. A laryngeal airway kit according to claim 17, wherein the outer edge of said first slide rail is parallel to the outer edge of said second slide rail.

21. An introducer for tracking a laryngeal airway device into the throat of a person, said introducer comprising:
- a curved blade having a proximal end, a distal end, an anterior side, and a posterior side;
- a blade tip connected to said distal end of said curved blade, said blade tip having a laterally curved shape, a distal end, an anterior side, and a posterior side; and
- a guide trough defined by said posterior side of said curved blade and by said posterior side of said blade tip, said guide trough extending from near said proximal end of said curved blade to said distal end of said blade tip.

22. An introducer according to claim 21, wherein said laterally curved shape of said blade tip has an apex at said anterior side of said blade tip.

23. An introducer according to claim 21, further comprising:
- a first slide rail connected to a first longitudinal edge of said curved blade, said first slide rail extending from near said proximal end of said curved blade to near said distal end of said curved blade; and
- a second slide rail connected to a second longitudinal edge of said curved blade, said second slide rail extending from near said proximal end of said curved blade to near said distal end of said curved blade.

* * * * *